(12) United States Patent
Parks et al.

(10) Patent No.: US 6,673,572 B2
(45) Date of Patent: Jan. 6, 2004

(54) METHODS FOR RESCUE OF RNA VIRUSES

(75) Inventors: Christopher L. Parks, Boonton, NJ (US); Mohinderjit S. Sidhu, Scotch Plains, NJ (US); Stephen A. Udem, New York, NY (US); Gerald R. Kovacs, Morristown, NJ (US)

(73) Assignee: Wyeth Holdings Corporation, Madison, NJ (US)

( * ) Notice: Subject to any disclaimer, the term of this patent is extended or adjusted under 35 U.S.C. 154(b) by 0 days.

(21) Appl. No.: 10/261,961

(22) Filed: Oct. 1, 2002

(65) Prior Publication Data

US 2003/0129729 A1 Jul. 10, 2003

Related U.S. Application Data

(63) Continuation of application No. 09/701,671, filed as application No. PCT/US99/12292 on Jun. 3, 1999, now abandoned.
(60) Provisional application No. 60/087,800, filed on Jun. 3, 1998.
(51) Int. Cl.[7] .................... C12P 21/06; C12Q 1/70; C12Q 1/68; A61K 39/00; A61K 39/12
(52) U.S. Cl. ................ 435/69.1; 435/5; 435/6; 435/325; 424/192.1; 424/199.1
(58) Field of Search ................ 435/5, 6, 69.1, 435/325; 424/192.1, 199.1

(56) References Cited

PUBLICATIONS

References cited in the parent application, 09/701,671.*

* cited by examiner

*Primary Examiner*—Hankyel T. Park
(74) *Attorney, Agent, or Firm*—Darryl L. Webster; Alan M. Gordon

(57) ABSTRACT

This invention relates to improved methods for producing nonsegmented, negative-sense, single-stranded RNA viruses of the Order designated Mononegavirales virus, including embodiments relating to methods of producing such viruses as attenuated and/or infectious viruses, such as Measles virus (MV) and respiratory syncytial virus (RSV). One method for producing a recombinant virus from the Order Mononegavirales comprises (a) in at least one host cell, conducting transfection of a rescue composition which comprises (i) a transcription vector comprising an isolated nucleic acid molecule which comprises polynucleotide sequence encoding a genome or antigenome of a nonsegmented, negative-sense, single stranded RNA virus of the Order Mononegavirales and (ii) at least one expression vector which comprises at least one isolated nucleic acid molecule encoding the trans-acting proteins necessary for encapsidation, transcription and replication; in a host cell under conditions sufficient to permit the co-expression of these vectors and the production of the recombinant virus; (b) heating the transfected rescue composition to an effective heat shock temperature under conditions sufficient to increase the recovery of the recombinant virus; and optionally, (c) harvesting the resulting recombinant virus.

81 Claims, 6 Drawing Sheets

RESCUE PROTOCOL

TRANSFECT 293-3-46 CELLS WITH
MV GENOMIC cDNA PLASMID AND
L EXPRESSION PLASMID

↓ 14-16 h

REPLACE TRANSFECTION MEDIA.
HEAT SHOCK 3h AT 44°C.

↓ 72 h AFTER START OF TRANSFECTION

TRANSFER TRANSFECTED CELLS FROM
ONE WELL OF SIX-WELL DISH TO A VERO CELL
MONOLAYER IN A 10cm DISH.

↓ 3-5 DAYS AFTER TRANSFER TO 10cm DISH

COUNT PLAQUES
HARVEST RECOMBINANT VIRUS

FIG. 1

| TRANSFECTION | EXP 1 | EXP 2 | EXP 3 | EXP 4 | EXP 5 | EXP 6 | |
|---|---|---|---|---|---|---|---|
| 1 | 0 | 0 | 0 | 22 | 14 | 0 | |
| 2 | 0 | 0 | 2 | 0 | 0 | 5 | |
| 3 | 0 | 3 | 0 | 3 | 37 | 15 | |
| 4 | 0 | 1 | 0 | 6 | 0 | 49 | |
| 5 | 0 | 50+ | 1 | 9 | 0 | 0 | NO HEAT SHOCK |
| 6 | 0 | 0 | 0 | 6 | 0 | 0 | |
| 7 | | | 0 | 0 | 0 | 50+ | |
| 8 | | | 0 | 7 | 2 | 1 | |
| 9 | | | 0 | 50+ | 1 | 0 | |
| 10 | | | 0 | 1 | 16 | 1 | |
| 11 | | | 1 | 1 | 0 | 0 | |
| 12 | | | 0 | 50+ | 0 | 0 | |
| 13 | + | 50+ | 1 | 50+ | 11 | 50+ | |
| 14 | + | 50+ | 50+ | 50+ | 50+ | 50+ | |
| 15 | + | 50+ | 4 | 50+ | 50+ | 13 | |
| 16 | + | 0 | 4 | 14 | 50+ | 1 | |
| 17 | + | 50+ | 50+ | 29 | 50+ | 0 | |
| 18 | + | 4 | 50+ | 50+ | 18 | 5 | HEAT SHOCK |
| 19 | + | | 1 | 32 | 50+ | 50+ | |
| 20 | + | | 50+ | 50+ | 50+ | 1 | |
| 21 | + | | 3 | 50+ | 50+ | 41 | |
| 22 | + | | 10 | 4 | 50+ | 2 | |
| 23 | + | | 3 | 50+ | 50+ | 50+ | |
| 24 | + | | 8 | 50+ | 50+ | 15 | |

FIG.5

METHODS FOR RESCUE OF RNA VIRUSES

This is a continuation of application Ser. No. 09/701,671 filed on Feb. 28, 2001 now abandoned, which the national Stage of International Application No. PCT/US99/12292, field Jun. 3, 1999, which claims the benefit of U.S. Provisional Application No. 60/087,800, filed Jun. 3, 1998, the entire disclosures of which are hereby incorporated by reference.

FIELD OF THE INVENTION

This invention relates to improved methods for producing nonsegmented, negative-sense, single-stranded RNA viruses of the Order designated Mononegavirales virus. Preferred embodiments relate to methods of producing such viruses as attenuated and/or infectious viruses, such as Measles virus (MV) respiratory syncytial virus (RSV) and Human parainfluenza virus (PIV). The recombinant viruses can be prepared from cDNA clones, and, accordingly, viruses having defined changes in the genome can be obtained.

BACKGROUND OF THE INVENTION

Enveloped, negative-sense, single stranded RNA viruses are uniquely organized and expressed. The genomic RNA of negative-sense, single stranded viruses serves two template functions in the context of a nucleocapsid: as a template for the synthesis of messenger RNAs (mRNAs) and as a template for the synthesis of the antigenome (+) strand. Negative-sense, single stranded RNA viruses encode and package their own RNA-dependent RNA Polymerase. Messenger RNAs are only synthesized once the virus has entered the cytoplasm of the infected cell. Viral replication occurs after synthesis of the mRNAs and requires the continuous synthesis of viral proteins. The newly synthesized antigenome (+) strand serves as the template for generating further copies of the (−) strand genomic RNA.

The polymerase complex actuates and achieves transcription and replication by engaging the cis-acting signals at the 3' end of the genome, in particular, the promoter region. Viral genes are then transcribed from the genome template unidirectionally from its 3' to its 5' end. There is always less mRNA made from the downstream genes (e.g., the polymerase gene (L)) relative to their upstream neighbors (i.e., the nucleoprotein gene (N)). Therefore, there is always a gradient of mRNA abundance according to the position of the genes relative to the 3'-end of the genome.

Molecular genetic analysis of such nonsegmented RNA viruses has proved difficult until recently because naked genomic RNA or RNA produced intracellularly from a transfected plasmid is not infectious (Boyer and Haenni, 1994). This technical problem has been overcome through development of clever cDNA rescue technology that permits isolation of recombinant nonsegmented, negative-strand RNA viruses (Pattnaik et al., 1992; Schnell, Mebatsion, and Conzelmann, 1994). The techniques for rescue of these different negative-strand viruses follows a common theme, each having distinguishing requisite components for successful rescue (Baron and Barrett, 1997; Collins et al., 1995; Garcin et al., 1995; Hoffman and Banerjee, 1997; Lawson et al., 1995; Radecke et al., 1995; Schneider et al., 1997; He et al, 1997; Schnell, Mebatsion and Conzelmann, 1994; Whelan et al., 1995). After transfection of a genomic cDNA plasmid, an exact copy of genome RNA is produced by the combined action of phage T7 RNA polymerase and a vector-encoded ribozyme sequence that cleaves the RNA to form the 3' termini. This RNA is packaged and replicated by viral proteins initially supplied by co-transfected expression plasmids. In the case of the Measles virus (MV) rescue system (Radecke et al., 1995), a stable cell line was prepared that expresses T7 RNA polymerase and the MV proteins N (nucleocapsid protein) and P (phosphoprotein polymerase subunit). Thus, MV rescue can be achieved by co-transfecting this cell line with an MV genomic cDNA clone containing an appropriately positioned T7 polymerase promoter and an expression plasmid that contains the MV polymerase gene (L).

Successful measles virus cDNA rescue apparently requires numerous molecular events to occur after transfection including: 1) accurate, full-length synthesis of genome RNA by T7 RNA polymerase and 3' end processing by the ribozyme sequence; 2) synthesis of viral N, P, and L proteins at levels appropriate to initiate replication; 3) the de novo packaging of genomic RNA into transcriptionally-active and replication-competent nucleocapsid structures; and 4) expression of viral genes from newly-formed nucleocapsids at levels sufficient for replication to progress. Exactly what steps may be rate-limiting in successful rescue has not been determined, but the efficiency of rescue potentially may be improved by stimulating any one of the steps mentioned above.

The present invention seeks to improve the ability to recover the desired recombinant RNA viruses, such as MV. It is submitted that the ability to obtain replicating virus from rescue may diminish as the polynucleotide, which encodes the native genome and antigenome of a desired virus, is increasingly modified. Accordingly, the present invention seeks to overcome such an obstacle since these methods can substantially improve the likelihood of obtaining a desired recombinant virus from a rescue procedure.

SUMMARY OF THE INVENTION

The present invention provides for a method for producing a recombinant virus from the Order Mononegavirales comprising; (a) in at least one host cell, conducting transfection of a rescue composition which comprises (i) a transcription vector comprising an isolated nucleic acid molecule which comprises a polynucleotide sequence encoding a genome or antigenome of a nonsegmented, negative-sense, single stranded RNA virus of the Order Mononegavirales and (ii) at least one expression vector which comprises at least one isolated nucleic acid molecule encoding the trans-acting proteins necessary for encapsidation, transcription and replication; in a host cell under conditions sufficient to permit the co-expression of these vectors and the production of the recombinant virus; (b) heating the transfected rescue composition to an effective heat shock temperature under conditions sufficient to increase the recovery of the recombinant virus; and optionally, (c) harvesting the resulting recombinant virus.

An additional method relates to producing a recombinant Mononegavirales virus comprising; a) in at least one host cell, conducting transfection of a rescue composition which comprises (i) a transcription vector comprising an isolated nucleic acid molecule encoding a genome or antigenome of a nonsegmented, negative-sense, single stranded RNA virus of the Order Mononegavirales and (ii) at least one expression vector which comprises at least one isolated nucleic acid molecule which comprises a polynucleotide sequence encoding the trans-acting proteins necessary for encapsidation, transcription and replication under conditions sufficient to permit the co-expression of said vectors and the production of the recombinant virus; b) transferring the transfected rescue composition onto at least one layer of Vero cells; and optionally, harvesting the recombinant virus.

Further aspects of the present invention relate to methods combining the non-overlapping steps of the above methods, along with preferred embodiments, to create further improved methods.

In alternative embodiments, this invention provides a method for making RNA viruses of the Order Mononegavirales which are attenuated, infectious or both. Additional embodiments relate to the viruses produced from the methods of this invention, as well as vaccines containing such viruses. It is noted that such viruses may be human or non-human, such as murine or bovine.

The above-identified embodiments and additional embodiments, which are discussed in detail herein, represent the objects of this invention.

BRIEF DESCRIPTION OF THE FIGURES

FIG. 1 depicts a flow diagram of modified rescue procedure. This procedure includes the use of a heat shock step and transferring transfected cells to a monolayer of Vero cells.

FIG. 5 is a table (Table 1) depicting the plaque counts from six independent rescue experiments that were performed to test the effect of heat shock as described in Example 2. The advantage of the heat shock procedure is clearly shown.

DETAILED DESCRIPTION OF THE INVENTION

Figure 2:
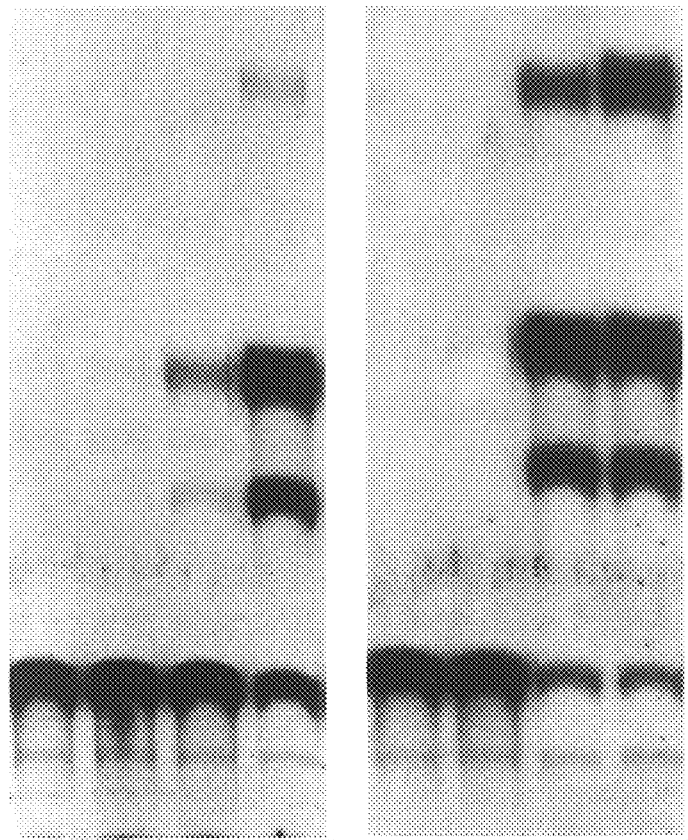
FIG. 2 is an autoradiogram showing the effect of heat shock on minireplicon gene expression from Example 4 through the use of CAT assays.
Figure 3:
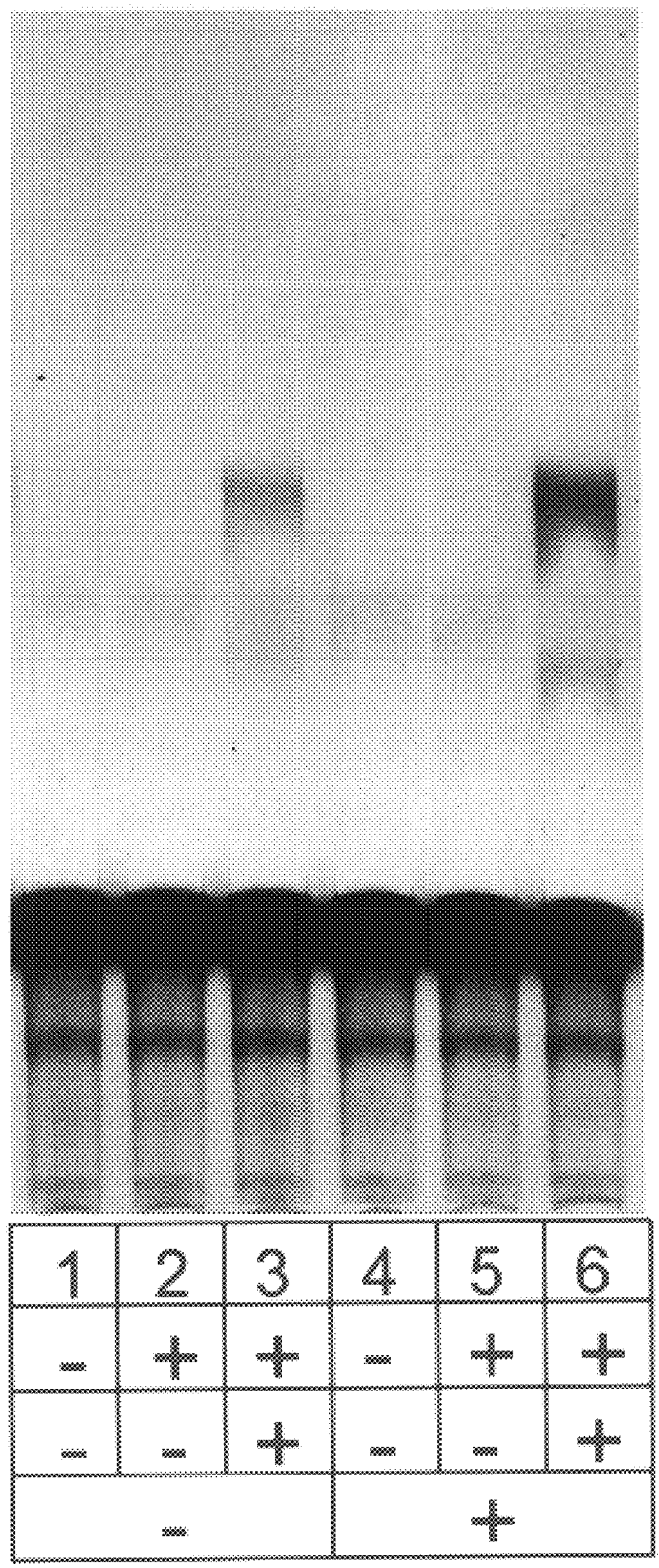
FIG. 3 is an autoradiogram showing the results of CAT assays for the minireplicon RNA transfection experiments of Example 5.

As briefly noted above, the present invention relates to a novel method of producing recombinant RNA virus. Such methods in the art are referred to as "rescue" or reverse genetics methods. Exemplary rescue methods for different nonsegmented, negative-strand viruses are disclosed in the following referenced publications: Baron and Barrett, 1997; Collins et al., 1995; Garcin et al, 1995; He et al., 1997; Hoffman and Banerjee, 1997; Lawson et al., 1995; Radecke and Billeter, 1997; Radecke et al., 1995; Schneider et al., 1997; Schnell, Mebatsion, and Conzelmann, 1994; Whelan et al., 1995. Additional publications on rescue include published International patent application WO 97/06270 for MV and other viruses of the subfamily Paramyxovirinae, and for RSV rescue, published International patent application WO 97/12032; these applications are hereby incorporated by reference.

After transfection of a genomic cDNA plasmid, an exact copy of genome RNA is produced by the combined action of phage T7 RNA polymerase and a vector-encoded ribozyme sequence that cleaves the RNA to form the 3' termini. This RNA is packaged and replicated by viral proteins initially supplied by co-transfected expression plasmids. In the case of the MV rescue system (Radecke et al., 1995), a stable cell line was prepared that expresses T7 RNA polymerase and the MV proteins N (nucleocapsid protein) and P (phosphoprotein). Thus, MV rescue can be achieved by co-transfecting this cell line with an MV genomic cDNA clone containing an appropriately positioned T7 polymerase promoter and an expression plasmid that contains the MV polymerase gene (L).

One of the first few rescue methods was disclosed for Measles virus. Measles virus (MV) is a member of the Morbillivirus genus in the Paramyxoviridae family, and like all members of this family, MV is an enveloped virus that contains a nonsegmented, negative-sense RNA genome (Lamb and Kolakofsky, 1996). Molecular genetic analysis of this family of viruses has proved difficult until recently because naked genomic RNA or RNA produced intracellularly from a transfected plasmid is not infectious (Boyer and Haenni, 1994). This technical problem has been overcome through development of clever cDNA rescue technology that permits isolation of recombinant negative-strand RNA viruses (Pattnaik et al., 1992; Radecke and Billeter, 1997; Schnell, Mebatsion, and Conzelmann, 1994).

A brief overview of a basic steps of these rescue methods and compositions therein is further described below:

Transcription and replication of negative-sense, single stranded RNA viral genomes are achieved through the enzymatic activity of a multimeric protein acting on the ribonucleoprotein core (nucleocapsid). Naked genomic RNA cannot serve as a template. Instead, these genomic sequences are recognized only when they are entirely encapsidated by the N protein into the nucleocapsid structure. It is only in that context that the genomic and antigenomic terminal promoter sequences are recognized to initiate the transcriptional or replication pathways.

All paramyxoviruses require three viral proteins N, P and L, for these polymerase pathways to proceed. The pneumoviruses, including RSV, also require the transcription elongation factor, M2, for the transcriptional pathway to proceed efficiently. Additional cofactors may also play a role, including perhaps the virus-encoded NS1 and NS2 proteins, as well as perhaps host-cell encoded proteins.

Briefly, all Mononegavirales rescue methods can be summarized as follows: Each requires a cloned DNA equivalent of the desired viral genome placed between a suitable DNA-dependent RNA polymerase promoter (e.g., the T7 RNA polymerase promoter) and a self-cleaving ribozyme sequence (e.g., the hepatitis delta ribozyme) which is inserted into a suitable transcription vector (e.g a propagatable bacterial plasmid). This transcription vector provides the readily manipulable DNA template from which the RNA polymerase (e.g., T7 RNA polymerase) can faithfully transcribe a single-stranded RNA copy of the viral antigenome (or genome) with the precise, or nearly precise, 5' and 3' termini. The orientation of the viral genomic DNA copy and the flanking promoter and ribozyme sequences determine whether antigenome or genome RNA equivalents are transcribed. Also required for rescue of new virus progeny are the virus-specific trans-acting proteins needed to encapsidate the naked, single-stranded viral antigenome or genome RNA transcripts into functional nucleocapsid templates: the viral nucleocapsid (N or NP) protein, the polymerase-associated phosphoprotein (P) and the polymerase (L) protein. These proteins comprise the active viral RNA-dependent RNA polymerase which must engage this nucleocapsid template to achieve transcription and replication. Certain viruses selected for rescue may require additional proteins, such as a transcription elongation factor.

Accordingly, in each method one will employ a rescue composition. Such compositions are well known in the art. The following description is not limitative of rescue compositions which can be employed in the methods of this invention. The rescue composition comprises (i) a transcription vector comprising an isolated nucleic acid molecule which comprises a polynucleotide sequence encoding a genome or antigenome of a nonsegmented, negative-sense, single stranded RNA virus of the Order Mononegavirales and (ii) at least one expression vector which comprises at least one isolated nucleic acid molecule encoding the trans-acting proteins necessary for encapsidation, transcription and replication; in a host cell under conditions sufficient to permit the co-expression of these vectors and the production of the recombinant virus.

The isolated nucleic acid molecule comprises a sequence which encodes at least one genome or antigenome of a nonsegmented, negative-sense, single stranded RNA virus of the Order Mononegavirales. Based on the revised reclassification in 1993 by the International Committee on the Taxonomy of Viruses, an Order, designated Mononegavirales, has been established. This Order contains three families of enveloped viruses with single stranded, nonsegmented RNA genomes, of minus polarity (negative-sense). These families are the Paramyxoviridae, Rhabdoviridae and Filoviridae. The family Paramyxoviridae has been further divided into two subfamilies, Paramyxovirinae and Pneumovirinae. The subfamily Paramyxovirinae contains three genera, Respirovirus (formerly known as Paramyxovirus), Rubulavirus and Morbillivirus. The subfamily Pneumovirinae contains the genus Pneumovirus.

The new classification is based upon morphological criteria, the organization of the viral genome, biological activities and the sequence relatedness of the genes and gene products. The morphological distinguishing feature among enveloped viruses for the subfamily Paramyxovirinae is the size and shape of the nucleocapsids (diameter 18 nm, 1 μm in length, pitch of 5.5 nm), which have a left-handed helical symmetry. The biological criteria are: 1) antigenic cross-reactivity between members of a genus, and 2) the presence of neuraminidase activity in the genera Respirovirus, Rubulavirus and its absence in genus Morbillivirus. In addition, variations in the coding potential of the P gene are considered, as is the presence of an extra gene (SH) in Rubulaviruses.

Pneumoviruses can be distinguished from Paramyxovirinae morphologically because they contain narrow nucleocapsids. In addition, pneumoviruses have major differences in the number of protein-encoding cistrons (10 in pneumoviruses versus 6 in Paramyxovirinae) and an attachment protein (G) that is very different from that of Paramyxovirinae. Although the paramyxoviruses and pneumoviruses have six proteins that appear to correspond in function (N, P, M, G/H/HN, F and L), only the latter two proteins exhibit significant sequence relatedness between the two subfamilies. Several pneumoviral proteins lack counterparts in most of the paramyxoviruses, namely the nonstructural proteins NS1 and NS2, the small hydrophobic protein SH, and a second protein M2. Some paramyxoviral proteins, namely C and V, lack counterparts in pneumoviruses. However, the basic genomic organization of pneumoviruses and paramyxoviruses is the same. The same is true of rhabdoviruses and filoviruses. Table 1 presents the current taxonomical classification of these viruses, together with examples of each genus.

TABLE 1

Classification of Nonsegmented, negative-sense, single stranded RNA Viruses of the Order Mononegavirales Family Paramyxoviridae Subfamily Paramyxovirinae

| | |
|---|---|
| Genus Respirovirus (formerly known as Paramyxovirus) | Sendai virus (mouse parainfluenza virus type 1) Human parainfluenza virus (PIV) types 1 and 3 Bovine parainfluenza virus (BPV) type 3 |
| Genus Rubulavirus | Simian virus 5 (SV5) (Canine parainfluenza virus type 2) Mumps virus Newcastle disease virus (NDV) (avian Paramyxovirus 1) Human parainfluenza virus (PIV-types 2, 4a and 4b) |
| Genus Morbillivirus | Measles virus (MV) Dolphin Morbillivirus Canine distemper virus (CDV) Peste-des-petits-ruminants virus Phocine distemper virus Rinderpest virus |

Subfamily Pneumovirinae

| | |
|---|---|
| Genus Pneumovirus | Human respiratory syncytial virus (RSV) Bovine respiratory syncytial virus Pneumonia virus of mice Turkey rhinotracheitis virus |

Family Rhabdoviridae

| | |
|---|---|
| Genus Lyssavirus | Rabies virus |
| Genus Vesiculovirus | Vesicular stomatitis virus (VSV) |
| Genus Ephemerovirus | Bovine ephemeral fever virus |

Family Filovirdae

| | |
|---|---|
| Genus Filovirus | Marburg virus |

As noted above, the isolated nucleic acid molecule comprises a sequence which encodes at least one genome or antigenome of a nonsegmented, negative-sense, single stranded RNA virus of the Order Mononegavirales. The isolated nucleic acid molecule may comprise a polynucleotide sequence which encodes a genome, antigenome or a modified version thereof. In one embodiment, the polynucleotide encodes an operably linked promoter, the desired genome or antigenome and a transcriptional terminator.

In a preferred embodiment of this invention the polynucleotide encodes a genome or anti-genome that has been modified from a wild-type RNA virus by a nucleotide insertion, rearrangement, deletion or substitution. It is submitted that the ability to obtain replicating virus from rescue may diminish as the polynucleotide encoding the native genome and antigenome is increasingly modified. In such instances, the present invention is particularly valuable since these methods can substantially improve the likelihood of recombinant virus rescue. The genome or antigenome sequence can be derived from that of a human or non-human virus. The polynucleotide sequence may also encode a chimeric genome formed from recombinantly joining a genome or antigenome from two or more sources. For example, one or more genes from the A group of RSV are inserted in place of the corresponding genes of the B group of RSV; or one or more genes from bovine PIV (BPIV), PIV-1 or PIV-2 are inserted in the place of the corresponding genes of PIV-3; or RSV may replace genes of PIV and so forth. In additional embodiments, the polynucleotide encodes a genome or anti-genome for an RNA virus of the Order Mononegavirales which is a human, bovine or murine virus. Since the recombinant viruses formed by the methods of this invention can be employed as tools in diagnostic research studies or as therapeutic or prophylactic vaccines, the polynucleotide may also encode a wild type or an attenuated form of the RNA virus selected. In many embodiments, the polynucleotide encodes an attenuated, infectious form of the RNA virus. In particularly preferred embodiments, the polynucleotide encodes a genome or antigenome of a nonsegmented, negative-sense, single stranded RNA virus of the Order Mononegavirales having at least one attenuating mutation in the 3' genomic promoter region and having at least one attenuating mutation in the RNA polymerase gene, as described by published International patent application WO 98/13501, which is hereby incorporated by reference.

The various needs for producing a recombinant virus may vary. Accordingly, one may select one more viruses from any particular Family: the Paramyxoviridae Family, the Rhabdoviridae Family or the Filoviridae Family.

In addition to polynucleotide sequences encoding the modified forms of the desired genome and antigenome as described above, the polynucleotide sequence may also encode the desired genome or antigenome along with one or more heterologous genes. The heterologous genes can vary as desired. Depending on the application of the desired recombinant virus, the heterologous gene may encode a co-factor, cytokine (such as an interleukin), a T-helper epitope, a restriction marker, adjuvant, or a protein of a different microbial pathogen (e.g. virus, bacterium or fungus), especially proteins capable of eliciting a protective immune response. The heterologous gene may also be used to provide agents which are used for gene therapy. In preferred embodiments, the heterologous genes encode cytokines, such as interleukin-12, which are selected to improve the prophylatic or therapeutic characteristics of the recombinant virus.

In view of some of the current needs for improved vaccines and increased flexibility in treating viral pathogens, the isolated nucleic acid molecule comprises a polynucleotide which encodes an RNA virus selected from the group consisting of CDV, VSV, MV, RSV, PIV, Mumps virus and rabies virus. Further preferences among this set of RNA viruses is the group consisting of MV, RSV, PIV and BPV.

For embodiments employing attenuated viruses, numerous forms of such viruses are well-known in the art, along with basic methods for introducing attenuating mutations to generate a modified virus. Conventional means are used, such as chemical mutagenesis during virus growth in cell cultures to which a chemical mutagen has been added, followed by selection of virus that has been subjected to passage at suboptimal temperature in order to select temperature sensitive and/or cold adapted mutations, identification of mutant virus that produce small plaques in cell culture, and passage through heterologous hosts to select for host range mutations. An alternative means of introducing attenuating mutations comprises making predetermined mutations using site-directed mutagenesis. One or more mutations may be introduced. These viruses are then screened for attenuation of their biological activity in an animal model. Attenuated viruses are subjected to nucleotide sequencing to locate the sites of attenuating mutations.

The various trans-acting proteins required for performing rescue are also well known in the art. The trans-acting proteins required for measles virus rescue are the encapsidating protein N, and the polymerase complex proteins, P and L. For PIV-3, the encapsidating protein is designated NP, and the polymerase complex proteins are also referred to as P and L. For RSV, the virus-specific trans-acting proteins include N, P and L, plus an additional protein, M2, the RSV-encoded transcription elongation factor.

The viral trans-acting proteins can be generated from one or more expression vectors (e.g. plasmids) encoding the required proteins, although some or all of the required trans-acting proteins may be produced within the selected host cell engineered to contain and express these virus-specific genes and gene products as stable transformants.

The choice of expression vector as well as the isolated nucleic acid molecule which encodes the trans-acting proteins necessary for encapsidation, transcription and replication can vary depending on the selection of the desired virus. The expression vectors are prepared in order to permit their co-expression with the transcription vector(s) in the host cell and the production of the recombinant virus under selected conditions.

The typical (although not necessarily exclusive) circumstances for rescue include an appropriate mammalian cell milieu in which T7 polymerase is present to drive transcription of the antigenomic (or genomic) single-stranded RNA from the viral genomic cDNA-containing transcription vector. Either cotranscriptionally or shortly thereafter, this viral antigenome (or genome) RNA transcript is encapsidated into functional templates by the nucleocapsid protein and engaged by the required polymerase components produced concurrently from co-transfected expression plasmids encoding the required virus-specific trans-acting proteins. These events and processes lead to the, prerequisite transcription of viral mRNAs, the replication and amplification of new genomes and, thereby, the production of novel viral progeny, i.e., rescue.

For the rescue of rabies, VSV, SV5 and Sendai, T7 polymerase is provided by recombinant vaccinia virus VTF7-3. This system, however, requires that the rescued virus be separated from the vaccinia virus by physical or biochemical means or by repeated passaging in cells or tissues that are not a good host for poxvirus. For MV cDNA rescue, this requirement is avoided by creating a cell line that expresses T7 polymerase, as well as viral N and P proteins. Rescue is achieved by transfecting the genome expression vector and the L gene expression vector into the helper cell line. Preferably, the helper cell line produces little or no progeny virus in mammalian cells and can be exploited to rescue the desired RNA virus or viruses. The helper virus can be used as a source of T7 polymerase, for example MVA/T7 (described infra). After simultaneous expression of the necessary encapsidating proteins, synthetic full length antigenomic viral RNA are encapsidated, replicated and transcribed by viral polymerase proteins and replicated genomes are packaged into infectious virions. In addition to such antigenomes, genome analogs have now been successfully rescued for Sendai and PIV-3 (Kato et al. and published International patent application WO 98/53708).

As noted above, MVA/M7 (a mutant attenuated of the vaccina virus) is an example of a modified helper virus which may be employed in the rescue of an RNA virus rescue. Generally, the modified helper virus is a virus which has been altered from a wild type virus to exhibit diminished, or no, viral activity in non-permissive cell lines. The characteristics of MVA establish the characteristics preferred in a modified helper virus. The MVA strain of vaccinia virus provides an attractive alternative to the more cytopathic strains. MVA was developed during the smallpox eradication program in Turkey and Germany by serial passages (>570) of the cytopathic vaccinia Ankara virus in chick embryo fibroblasts. It has been downgraded to a Biosafety Level-1 pathogen, and may be used by unvaccinated laboratory workers. MVA contains six major deletions (>15% of the genome) resulting in a loss of over 30,000 basepairs (Antoine et al., 1998). MVA replicates in a limited number of cell lines (Carroll and Moss, 1997; Drexler et al., 1998), and is blocked at a late stage in viral morphogenesis in nonpermissive cells (Sutter and Moss, 1992). Moreover, MVA does not induce the severe cytopathic effect (CPE) observed with the wild type strains. A major advantage of MVA over other host-restricted poxviruses (e.g. NYVAC, ALVAC, and fowlpox) is that viral DNA replication, and thus the transcription of almost all gene classes (early, intermediate and late) is unimpaired. Foreign genes may be efficiently expressed under all classes of promoters. Two recombinant MVAs expressing the bacteriophage T7-gene 1 have been reported. The MVA/T7 hybrid viruses contain one integrated copy of the T7 gene-1 under the regulation of either the 7.5K weak early/late promoter (Sutter et al., 1995) or the 11K strong late promoter (Wyatt et al., 1995). Both have been used as helper viruses in transient expression systems to genetically rescue negative-stranded RNA viruses (Collins et al., 1995; Leyrer et al., 1998; Schneider et al., 1997; Barron, M. D. and Barrett, T. Rescue of rinderpest virus from a cloned cDNA. Journal of Virology. 71(2):1265–71, February 1997; Durbin, A. P., Hall, S. L., Siew, J. W., Whitehead, S. S., Collins, P. L., and Murphy, B. R. Recovery of infectious human parainfluenza virus type 3 from cDNA. Virology. 235(2): 323–332, 1997.; He et al., 1997).).

In spite of the benefits of employing a helper virus, such as an attenuated helper virus like MVA/T7, the concurrent replication cycle of MVA/T7 or another helper virus may suppress the genetic events that are required for the rescue of a heterologous recombinant virus. Accordingly, in preferred embodiments of this invention, when a helper virus is employed, a DNA synthesis inhibitor is also employed. This embodiment results in an improvement in the rescue system. A DNA synthesis inhibitor permits rescue to occur while also inhibiting (or substantially inhibiting) DNA synthesis of the helper virus. Exemplary DNA synthesis inhibitors, such as AraC (cytosine beta-D-arabinofuranoside) and hydroxyurea, block the replication cycle of the helper virus at a crucial point in the viral life cycle. Since intermediate and late viral gene transcription initiates only on nascent viral genomes, these two gene classes are silent as a result of blocking by AraC or hydroxyurea. AraC blocks replication by incorporating into DNA, while hydroxyurea inhibits ribonucleotide reductase reducing the cellular pool of deoxyribonucleotides. There are many additional DNA syntheisis inhibitors available. The additional DNA synthesis inhibitors are known to block cellular DNA synthesis but they are not recommended for use in blocking MVA replication. These include: DNA Polymerase inhibitors (like Aphidicolin), Topoisomerase inhibitors (examples like camptothecin blocks type I topoisomerases; Novobiocin and Nalidixic acid block type II topoisomerases) and DNA Gyrase inhibitors (like Heliquinomycin). The DNA synthesis inhibitors which block cellular DNA synthesis would be more effective for helper viruses that are heavily dependent upon cellular enzymes to perform replication functions.

A clear advantage of using DNA synthesis inhibitors during a genetic rescue event is that there should be very little or no contamination of the rescued RNA virus with a modified helper virus. In MVA, the replication cycle in nonpermissive cells is halted at very late stage in morphogenesis, resulting in viral particles that are noninfectious. Infection of semi-permissive cells results in limited viral growth, which is contraindicated in genetic rescue experiments. Under blocking by AraC or hydroxyurea, the concomitant inhibition of late protein synthesis results in the complete absence of viral particles. The rescued virus is directly amplified in a cell line that is permissive for growth of the helper virus. The amounts of DNA synthesis inhibitors used for transfection are readily determined by test experiments for analyzing growth of the helper virus.

The molecular events required for the conversion of a viral cDNA into a recombinant RNA virus are generally understood to involve the transcription by T7 polymerase and replication of either a negative- or positive-stranded full length genome by three or more viral trans-acting factors (N, P, and L, in the case of MV). The concurrent MVA replication results in the depletion of intracellular and extracellular resources throughout the rescue event, probably compromising it to some extent. Blocking the expression of intermediate and late genes results in the conservation of these resources, and is perhaps one reason why the genetic rescue in the presence of inhibitors is enhanced.

The cytopathic effect (CPE) induced by viral infection is markedly reduced in MVA-infected cells as compared to wild-type virus-infected cells. It is further reduced in MVA-infected cells treated with DNA synthesis inhibitors. Extending the life of the infected cell permits the expression of a wider variety foreign genes. This may be another advantageous component for improved genetic rescues.

The use of other promoters (strong early, early/intermediate, intermediate or early/late) to drive T7 expression can enhance genetic rescues, preferably in the presence of DNA replication inhibitors. Promoters of vaccina virus are suitable for the methods of this invention.

Host cells are then transformed or transfected with the at least two expression vectors described above. The host cells are cultured under conditions which permit the co-expression of these vectors so as to produce the infectious attenuated virus.

The rescued infectious virus is then tested for its desired phenotype (temperature sensitivity, cold adaptation, plaque morphology, and transcription and replication attenuation), first by in vitro means. The mutations at the cis-acting 3' genomic promoter region are also tested using the minireplicon system where the required trans-acting encapsidation and polymerase activities are provided by wild-type or vaccine helper viruses, or by plasmids expressing the N, P and different L genes harboring gene-specific attenuating mutations (Radecke et al. (1995) and Sidhu et al. (1995)).

If the attenuated phenotype of the rescued virus is present, challenge experiments are conducted with an appropriate animal model. Non-human primates provide the preferred animal model for the pathogenesis of human disease. These primates are first immunized with the attenuated, recombinantly-generated virus, then challenged with the wild-type form of the virus.

The host cells which can be employed in the rescue methods of this invention are those which permit the expression from the vectors of the requisite constituents necessary for the production of the desired recombinant virus. Such host cells can be selected from a prokaryotic cell or a eukaryotic cell, and preferably a vertebrate cell. In general, preferred host cells are derived from a human cell, such as a human embryonic kidney cell. Radecke et al. 1995 disclose the use of a host cell which is derived from a human embryonic kidney cell line designated as 293 3-46. Vero cells, as well as many other types of cells can also used as host cells. The following are examples suitable host cells: (1) Human Diploid Primary Cell Lines: e.g. WI-38 and MRC5 cells; (2) Monkey Diploid Cell Line: e.g. FRhL—Fetal Rhesus Lung cells; (3) Quasi-Primary Continues Cell Line: e.g. AGMK—african green monkey kidney cells.; (4) Human 293 cells (qualified) and (5) other potential cell lines, such as, CHO, MDCK (Madin-Darby Canine Kidney), primary chick embryo fibroblasts. In alternatively preferred embodiments, a transfection facilitating reagent is added to increase DNA uptake by cells. Many of these reagents are known in the art. LIPOFECTACE (Life Technologies, Gaithersburg, Md.) and EFFECTENE (Qiagen, Valencia, Calif.) are common examples. Lipofectace and Effectene are both cationic lipids. They both coat DNA and enhance DNA uptake by cells. Lipofectace forms a liposome that surrounds the DNA while Effectene coats the DNA but does not form a liposome.

Since many of the RNA viruses employed in this invention are human pathogens, a primate cell is preferably employed in such instances. There are exceptions such as canine distemper virus and other morbilliviruses that infect non-human mammals. All of these viruses infect only eukaryotic cells. Measles virus is primarily restricted to primate cell types. Some eukaryotic cell lines work better than others for propagating viruses and some cell lines do not work at all for some viruses. A cell line is employed that yields detectable cytopathic effect in order that rescue of viable virus may be easily detected. In the case of measles and potentially other viruses, the transfected cells are grown on Vero cells because the virus spreads rapidly on Vero cells and makes easily detectable plaques. This is another important feature of the invention. In general, a host cell which is permissive for growth of the selected virus is employed. In some instances, the host cell is a "complementing cell type". In the case of Measles virus, 293-3-46 cells (Radecke et al., 1995) are used because they express the N and P genes of Measles virus, as well as the T7 RNA polymerase gene. Other systems do not have this limitation because all necessary viral proteins are provided by expression plasmids and vaccinia virus which expresses T7 RNA polymerase.

The transcription vector and expression vector can be plasmid vectors designed for expression in the host cell. The expression vector which comprises at least one isolated nucleic acid molecule encoding the trans-acting proteins necessary for encapsidation, transcription and replication may express these proteins from the same expression vector or at least two different vectors. These vectors are generally known from the basic rescue methods, and they need not be altered for use in the improved methods of this invention.

In one improved method of the present invention, an effective heat shock temperature is used. An effective heat shock temperature is a temperature above the standard temperature suggested for performing rescue of a recombinant virus. In many instances, an effective heat shock temperature is above 37° C. When a rescue method is carried out at an effective heat shock temperature, the rescue method generates an increase in recovery of the desired recombinant virus over the level of recovery of recombinant virus when rescue is performed in the absence of the increase in temperature. The effective heat shock temperature and exposure time may vary based upon the rescue system used. Such temperature and time variances can result from the differences in the viral genome selected or host cell type. Although the temperature may vary, an effective heat shock temperature can be readily ascertained by conducting several test rescue procedures with a particular recombinant virus, and establishing a rate percentage of recovery of the desired recombinant virus as temperature and time of exposure are varied. Certainly, the upper end of any temperature range for performing rescue is the temperature at which the components of the transfection are destroyed or their ability to function in the transfection is depleted or diminished.

An exemplary list of temperature ranges are shown below:

from 38° C. to about 50° C., from 39° C. to about 49° C., from 39° C. to about 48° C. from about 40° C. to about 47° C., from about 41° C. to about 47° C., from about 41° C. to about 46° C., with from about 42° C. to about 46° C. being the more preferred. Alternatively, it is noted that heat shock temperatures of 43° C., 44° C., 45° C. and 46° C. are particularly preferred.

Without being bound by the following, it is hereby theorized that employing an elevated temperature for heat shock temperature during rescue triggers a cellular response and synthesis associated with heat shock proteins (referred to as hsps). It is recognized that heat shock induces the cellular stress response and the synthesis of a group of multifunctional proteins called the heat shock proteins (hsps) (Craig, 1985; Gunther and Walter, 1994; Lindquist, 1986). Many, but not all, of the hsps are encoded by highly inducible genes and these proteins are synthesized at elevated levels to help the cell recover from stress. The inducible hsps are also present in the cell at basal levels indicative of the various roles these proteins play in normal cell function. Some of the hsps are also called chaperones because they play an important role in assisting proper protein folding (Gething, 1996; Martin and Hartl, 1997). Other functions attributed to hsps include roles in protein trafficking in the cell, modulation of enzyme and protein function, participation in DNA replication, and involvement in viral replication and pathogensis (Franke, Yaun, and Luban, 1994; Friedman et al., 1984; Gething, 1996; Glick, 1995; Hu, Toft, and Seeger, 1997; Lund, 1995; Martin and Hartl, 1997; Pratt, 1992; Santoro, 1996).

The mammalian heat shock protein 70 (hsp70) -family is a related group of proteins of approximately 70 kD) in size. The major inducible form of hsp70 (hsp72) has an apparent molecular weight of 72 kD. The 73 kD hsp70 protein (hsp73) is expressed in the cell constitutively and has been termed a heat-shock cognate protein (hsc73, (Gunther and Walter, 1994)). These proteins participate in some of the functions mentioned above and have been implicated as one of the host cell factors that increases native (non-rescued) CDV gene expression in response to heat shock. The Hsp72 isoform copurifies with the fraction of CDV nucleocapsids that contain enhanced viral transcriptional activity (Oglesbee et al., 1996).

In view of our exemplary results as described herein, one can infer that the effect of heat shock temperature on CDV gene expression and the gene expression for other viruses which may be rescued in accordance with the methods described herein, is due to, at least in part, the induction of Hsp70s. Accordingly, alternative embodiments of this invention relate to the use of an effective heat shock temperature which is capable of effecting induction of hsps, especially an Hsp 70, such as Hsp 72.

In conducting the tests to establish the selected heat shock temperature, one can also select a desired time for performing the heat shock procedure. A sufficient time for applying the effective heat shock temperature is the time over which there is an increase in recovery of the desired recombinant virus over the level of recovery of recombinant virus when rescue is performed in the absence of an increase in temperature over the standard temperature suggested for conducting the rescue. The appropriate length of time may vary based upon the rescue system. Such variance in time can also result from the differences in the viral genome selected or host cell type. Although the time may vary, the amount of time for applying an effective heat shock temperature can be readily ascertained by conducting several test rescue procedures with a particular recombinant virus, and establishing a rate or percentage of recovery of the desired recombinant virus as temperature and time are varied. Certainly, the upper limit for any time variable used in performing rescue is the amount of time at which the components of the transfection are destroyed or their ability to function in the transfection is depleted or diminished. The amount of time for the heat shock procedure may vary from several minutes to several hours, as long as the desired increase in recovery of recombinant virus is obtained.

Although the time of exposure of the transfected cells to the effective heat shock temperature can vary with each rescue system, an exemplary list of exposure time ranges (in minutes) is shown below:

from about 5 to about 300, from about 15 to about 300, from 15 to about 240, from about 20 to about 200, from about 20 to about 150, with from about 30 to about 150 being the most preferred range.

Numerous means can be employed to determine the level of improved recovery of the desired recombinant virus. As noted in the examples herein, a chloramphenicol acetyl transferase (CAT) reporter gene can be used to monitor rescue of the recombinant virus. The corresponding activity of the reporter gene establishes the baseline and improved level of expression of the recombinant virus. Other methods include detecting the number of plaques of recombinant virus obtained and verifying production of the rescued virus by sequencing. The improved recovery should exhibit an increase of at least about 25% or at least about 40%. Preferably, the increase in the recombinant virus recovered is about 2-fold. About a 5- to 10-fold increase in the amount of recombinant virus has been observed.

One suggested method for determining the level of improved recovery of the desired recombinant virus involves preparing a number of identically transfected cell cultures and exposing them to different conditions of heat shock (time and temperature variable), and then comparing to control cells transfected and maintained at a constant temperature of 37° C. At 72 hours after transfection, the transfected cells are transferred to a 10 cm plate containing a monolayer of about 75% confluent Vero cells (or cell type of choice for determining plaque formation of the recombinant virus) and continuing incubation until plaques are visible. Thereafter, the plaques are counted and compared with the values obtained from control cells. Optimal heat shock conditions should maximize the number of plaques.

In another embodiment of the present invention, the transfected rescue composition, as present in the host cell(s), is subjected to a plaque expansion step or amplification step. This aspect of the present invention provides for an improved rescue method for producing a recombinant Mononegavirales virus, which method comprises; (a) in a host cell, conducting transfection of a rescue composition which comprises (i) a transcription vector comprising an isolated nucleic acid molecule encoding a genome or antigenome of a nonsegmented, negative-sense, single stranded RNA virus of the Order Mononegavirales and (ii) at least one expression vector which comprises at least one isolated nucleic acid molecule encoding the trans-acting proteins necessary for encapsidation, transcription and replication under conditions sufficient to permit the co-expression of said vectors and the production of the recombinant virus; (b) transferring the transfected rescue composition onto at least one layer of plaque expansion cells (PE cells); and (c) optionally, harvesting the recombinant virus. Often, the host cell employed in conducting the transfection is not favorable for growth of the desired recombinant virus. The recovery of recombinant virus from the transfected cells can be improved by selecting a plaque expansion cell in which the native virus or the recombinant virus exhibits enhanced growth. Any of the various plates or containers known in the art can be employed used for the plaque expansion step. Preferably, the transfected cels containing the rescue composition is transferred onto a monolayer of PE cells. In particular, the layer of PE cells should be at least about 50% confluent. Alternatively, the PE cells are least about 60% confluent or even at least about 75% confluent. In order to achieve plaque expansion, the transfected cells are transferred to containers of PE cells such that the surface area of the PE cells is greater than the surface area used for preparing the transfected virus. An enhanced surface area ratio of from 2:1 to 100:1 can be employed as desired. An enhanced surface area of at least 10:1 is preferred. The plaque expansion cells are selected based on the successful growth of the native or recombinant virus in such cells. Vero cells worked well in the exemplary experiments discussed herein, and, accordingly, they are preferred as PE cells.

Additional, improved rescue methods are achieved by replacing the transfection media prior to, or simultaneous with, a plaque expansion with Vero cells or a heat shock procedure. Media replacement can occur at various times before plaque expansion or heat shock temperature; however, replacing the media after about 4 to about 20 hours of incubating the transfected cells, can be followed as a starting point and then adjusted as desired thereafter from conducting test runs of the rescue method.

Segmented, Single-stranded RNA Viruses

Although one of the important aspects of the present invention is the application of these improved methods in the recovery of nonsegmented, negative sense, single-stranded, RNA viruses, the methods of this invention can be useful for enhancing the rescue of many types of RNA viruses, including segmented, negative sense, single stranded, RNA viruses. Based on the revised reclassification in 1993 by the International Committee on the Taxonomy of Viruses, the latter group of viruses belong to three families of viruses which are the Orthomyxoviridae, Bunyaviridae and Arenaviridae.

| Family Orthomyxoviridae | |
| --- | --- |
| Genus Influenzavirus A, B | Vertebrates, influenza A virus |
| Genus Influenzavirus C | Vertebrates, influenza C virus |
| Genus "unnamed, Thogoto-like virus" | Vertebrates: Thogoto virus |
| Family Bunyaviridae | |
| Genus Bunyavirus | Vertebrares: Bunyamwera virus |
| Genus Nairovirus | Vertebrates: Nairobi sheep virus |
| Genus PhlebOvirus | Vertebrates: sandfly fever Sicilian virus |
| Genus Hantavirus | Vertebrates: Hantaan virus |
| Genus Tospovirus | Plants: tomato spotted wilt virus |
| Family Arenaviridae | |
| Genus Arenavirus | Vertebrates: lymphocytic choriomeningitis virus |
| Genus Tenuivirus | Plants: rice stripe virus |

From these segmented virus Families, the viruses which present potential health risks to humans are of particular interest. Reverse genetics (or rescue) has provided a pathway for producing recombinant influenza A by assembling the virion RNA with an active transcriptase complex for the genome to initiate replication (Enami and Palase). The method involves in vitro transcription of a cDNA copy, creating a desired virus gene segment, native or mutated, into a copy of vRNA and recovering the virus. The vRNA is mixed with RNP proteins (obtained from purified virions) and then transfected into a cell with a helper virus (e.g. a wild-type virus corresponding to desired recombinant virus). For example, in preparing recombinant influenza A influenza A virus is employed to provide proteins which replicate the transfected RNA gene. A mixture of recombinant virus and helper virus are formed. Since the helper virus is present in great excess, a strong selection system, such as an antibody selection system, is employed to selectively separate progeny (Enami and Palase, 1991). The heat shock procedure of the present invention can be employed to increase the volume of the resulting mixture and the amount of recombinant virus obtained by subjecting the appropriate rescue composition, of RNA, RNPs and any additional components such as active transcriptase complexes when co-infection is conducted with the helper virus.

Specifically, the heat shock procedure of the present invention can also be employed to improve the efficiency of the procedure used to produce virus-like particles by packaging synthetic influenza-like CAT:RNA minigenome in the COS-1 cells, by vaccinia-T7 polymerase expressing cDNA clones of 10 influenza A virus-coded proteins (Mena et al, 1996). In an additional embodiment, the heat shock procedure of the present invention can be employed in improving the efficiency of a helper independent system for the rescue of a segmented, negative-strand RNA genome of Bunyamwera bunyavirus (Bridgen and Eliott, 1996). This system is similar to the one used for nonsegmented, negative sense RNA virus rescue experiments (rather than that described for rescue of the segmented influenza viruses). Plasmids containing full-length cDNA copies of the three Bunyamwera bunyavirus RNA genome segments were constructed and were flanked by T7 promoter and ribozyme sequences to generate genomic copies of the RNAs with the precise genomic termini. When cells expressing T7 polymerase and recombinant Bunyamwera bunyavirus proteins were transfected with these plasmids, full length antigenome RNAs were transcribed and encapsidated intracellularly, and these in turn were replicated and packaged into infectious bunyavirus particles.

The observations described herein that heat shock enhances rescue of recombinant MV and increases expression of the CAT reporter gene from MV minireplicons, combined with the results indicating that CDV L polymerase activity is stimulated by hsp72 (Oglesbee et al., 1996), gives rise to a belief that the induction of hsp72 may be substantially responsible for the effect of heat shock described herein. This possibility was examined by expressing one of the genes for hsp72 from an expression vector during CAT minireplicon experiments. Expression of an epitope-tagged version of the hsp protein was confirmed by western blot analysis (Example 6). The presence of the hsp expression vector increased CAT levels in transfected cells up to 20 fold (Example 6). These results suggest that high level expression of hsp72 may increase virus rescue efficiency. Furthermore, these results imply that a stable cell line that expresses high levels of hsp72 may be favorable for rescue. Ideally, the stable cell line would express the hsp72 from an inducible promoter such that the amount of expression of the hsp72 gene could be regulated. This would permit selecting an induction time period and induction level that would maximize rescue and also avoid any potentially toxic effects to the cell line of constitutive high-level expression of the hsp gene.

The recombinant viruses prepared from the methods of the present invention can be employed for diagnostic and therapeutic applications. Preferably, the recombinant viruses prepared from the methods of the present invention are used, alone or in conjunction with pharmaceuticals, antigens, immunizing agents or adjuvants, as vaccines in the prevention or amelioration of the viral disease. These active agents can be formulated and delivered by conventional means, i.e. by using a diluent or pharmaceutically-acceptable carrier.

The following examples are provided by way of illustration, and should not be construed as limitative of the invention as described hereinabove.

EXAMPLES

Methods and Materials

Cells, virus and transfection.

293-3-46 cells (Radecke et al., 1995) and 293 cells (Graham et al., 1977) were maintained in Dulbecco's modified minimal essential media (DMEM) supplemented with 10% fetal bovine serum (FBS). 293-3-46 cells were grown with selection in media containing G418 (Geneticin, Gibco-BRL) at 1.5 mg per ml. Vero cells were grown in DMEM containing 5% FBS, and HeLa suspension cells were grown in minimal essential media (SMEM) supplemented with 10% FBS. MV (Edmonston B) was propagated in HeLa suspension cultures as described earlier (Udem, 1984).

Transfections were performed using the calcium-phosphate precipitation method (Ausubel et al., 1987; Graham and van der Eb, 1973). 293-3-46 or 293 cells used for transfection were seeded onto 6 well plates and grown to about 50–75% confluence. Cells were fed 1–3 hours before transfection with 4.5 ml of fresh media lacking G418. Transfection mixtures were prepared by combining the appropriate DNAs in a final volume of 225 $\mu$l in water followed by adding 25 $\mu$l of 2.5M $CaCl_2$. The DNA-calcium mixture was vortexed gently while slowly adding 250 $\mu$l of 2×HEPES buffered saline (280 mM NaCl, 1.5 mM $Na_2HPO_4$, 50 mM HEPES, pH 7.05). The precipitate was allowed to stand at room temperature for 20 minutes then added to the cells. The cells were incubated overnight (14–16 hours), then the transfection media was removed and the cells were rinsed and fed with fresh media lacking G418. Infection of transfected cells was performed with 5 plaque forming units (pfu) per cell after removing the transfection media. Infections were incubated 2 hours before replacing the media. At this time, dishes containing cells that were to be heat shocked were wrapped in parafilm and transfered to a water bath at 44° C. and incubated 3 hours before being transferred to an incubator at 37° C. Cells were harvested at 48 hrs, after initiation of transfection for analysis of transient gene expression or harvested at 72 hours (or as otherwise noted herein) for rescue experiments. Chloramphenicol acetyl transferase (CAT) assays were performed as described previously (Sidhu et al, 1995. and Parks and Shenk, 1996).

Cells harvested for virus rescue were removed from the wells by repeated pipeting of the media over the monolayer to detach the cells and break the monolayer into small clumps. No cell dissociating agents were used. The cells and 5 ml of media were immediately distributed onto a near-confluent monolayer of Vero cells growing in 10 ml of media on a 10 cm dish. Four to five days later, plaques were visible and the monolayers were stained for plaque counting or harvested to prepare a recombinant virus stock.

RNA transfections were performed as described above for DNA with the following modification. RNA for transfection was prepared in vitro using the T7 RNA polymerase reagents in the Megascript kit (Ambion). RNA-calcium phosphate precipitates were incubated with 293 cells for 5–6 hours and then removed. Transfection and infection were carried out simultaneously by addition of virus to the transfection media. After replacing the transfection-infection media, appropriate cell samples were heat shocked at 43–44° C. The cells were harvested at 24–28 hours after the initiation of transfection/infection.

Recombinant DNA

The full-length MV cDNA plasmid (p(+) MV) and the MV L gene expression plasmid (pEMC-La) were generously provided by Martin Billeter and Frank Radecke (Radecke et al., 1995). Preparation of the CAT minireplicon has been described (Sidhu et al., 1995). The hsp70 expression plasmid was cloned by amplifying the cDNA (Hunt and Morimoto, 1985) from RNA extracted from heat shocked 293-3-46 cells. The reverse transcription-PCR (RT/PCR) reaction was performed with the high fidelity enzyme mixture containing Moloney Murine Leukemia Virus Reverse Transcriptase, Taq DNA polymerase and Pwo DNA polymerase found in the Titan kit reagents (Boehringer Mannheim). The hsp70 cDNA was cloned into the expression plasmid pCGN (Tanaka and Herr, 1990) to generate an expression construct containing the influenza HA epitope tag in the amino terminal coding region.

DNA Sequencing

The MV sequence was determined by sequencing DNA amplified by RT/PCR. RNA from MV infected cells was prepared by the guanidinium isothyocyanate-phenol-chloroform extraction method (Chomczynski and Sacchi., 1987) and RT/PCR was performed using reagents in the Titan kit (Boehringer Mannheim). Amplified DNA was gel purified in low melt agarose gels. The PCR fragment was sequenced using dye terminator reactions (Applied Biosystems) and analyzed on an ABI Prism™ automated sequencer (Perkin-Elmer). Sequence confirmation of plasmid DNAs was also performed with the automated sequencer.

Example 1 cDNA Rescue Protocol

This protocol is summarized in FIG. 1.

The day before starting the transfection, 293-3-46 cells are split into six-well plates using DMEM supplemented with 10% fetal bovine serum (FBS) and 1.5 mg/ml G418 antibiotic. One confluent 10 cm plate is split onto a six-well dish if use the next day is expected. Twelve wells per rescue experiment are transfected in order to increase the likelihood of recovering the recombinant virus.

At about one to three hours before transfection, replace media in each well with 4.5 ml DMEM supplemented with 10% FBS (No G418), and then initiate transfection.

Calcium-Phosphate Precipitate:

Water and DNA in a volume of 225 µl are combined in a sterile 5 ml polypropylene tube. Five (5) µg of p(+) MV and 100 ng of the L expression plasmid (pEMC-La) are used per transfection. Twenty-five (25) µl of 2.5M CaCl$_2$ are added and mixed. Two hundred fifty (250) µl of 2×HBS are added dropwise while gently vortexing the tube. After adding the HBS, the tubes stand at room temperature for 15–20 minutes (the HBS is 2×HEPES buffered saline: 280 mM NaCl, 1.5 mM Na$_2$HPO$_4$, 50 mM HEPES, pH 7.05 (Ausubel et al., 1987). It is helpful to set up individual transfections for each well rather than making a large master transfection mix. The precipitate is added dropwise to the media and the cells are incubated overnight for about 12 to 16 hours.

Then the media is removed and cells are washed. The cells are rinsed two times with a HEPES/saline solution (150 mM NaCl, 50 mM HEPES, 1 mM MgCl$_2$, pH7.2). Prior to incubating the cells, 5 ml of media (DMEM, 10% FBS, no G418) are added.

HEAT SHOCK: After adding fresh media as described above, the six-well plate is sealed with parafilm and transferred to a Tupperware container with a lid. The container is submerged in a water bath at 43–44° C. and incubated for 3 hours. After this heat shock step, the parafilm is removed from the plate and the cells are transferred to an incubator at 37° C. The cells are incubated for a total of about 72 hours after the start of the transfection.

After completing the incubation, a plaque expansion step is carried out with Vero cells. Vero cells are prepared the day before use by splitting one 10 cm plate to four or five 10 cm plates. After overnight incubation, the cells are about 75% confluent. Enough plates are prepared so there is one plate of Vero cells per transfected well. At about 72 hours after initiation of transfection, each well of transfected 293-3-46 cells are transferred to a 10 cm plate containing Vero cells. The 293-3-46 cells are transferred by repeated pipetting of the 5 ml of culture media over the cells to dislodge them from the well and break the monolayer into small cell clumps. Pipette gently to avoid cell lysis but forceful enough to dislodge the cells. The 5 ml of culture media containing the transfected cell clumps is then distributed into the 10 cm plate of Vero cells already containing 10 ml of culture media. Depending on the rescue system, one should allow sufficient time, about 4–5 days, to visualize plaques. The recombinant virus is harvested by scraping the cells and collecting them by centrifugation. The cells are resuspended in 1 ml of serum-free DMEM (Gibco/BRL) lacking serum and freeze-thawed once to release virus.

Example 2

In this example, the rescue method described in Example 1 was repeated six times, along with a control in which no heat shock was applied. Results from the six independent rescue experiments are shown in FIG. 5. The MV cDNA used in all experiments contained Edmonston B sequences (Radecke et al., 1995). Transfections were performed as described above and heat shock incubation was 3 hours at 44° C. Experiment 1 was scored plus or minus plaques, and in the remaining experiments plaques were counted. The experiments conducted in this example revealed the following:

The two modifications of the conventional rescue technique (Radecke et al., 1995), a heat shock step and a plaque expansion step, were each effective in increasing greatly the number of transfected cultures which produced recombinant virus. Before employing these modifications, only about 2–3% of the transfected cultures produced recombinant virus. In the above procedure, from 50 to about 90% of the transfected cultures produced recombinant virus.

Example 3

Plaque Expansion Modification

The plaque expansion step in the rescue protocol in Example 1 was established from the following type of experiments, which are conducted in the absence of a heat shock treatment.

Experiments were performed without the Plaque Expansion step of Example 2, while following the procedures outlined by Radecke et al. (1995). In these experiments, the transfected cells were transferred from a well in a six-well dish to a 10 cm plate to permit 4–5 days of additional cell growth and additional time for plaques to develop. No plaques were detected using this procedure. In the second type of experiment, the transfected cells were harvested by scraping and centrifugation and resuspended in serum-free OPTIMEM (Life Technologies, Gaithersburg, Md.) media.

Figure 4:
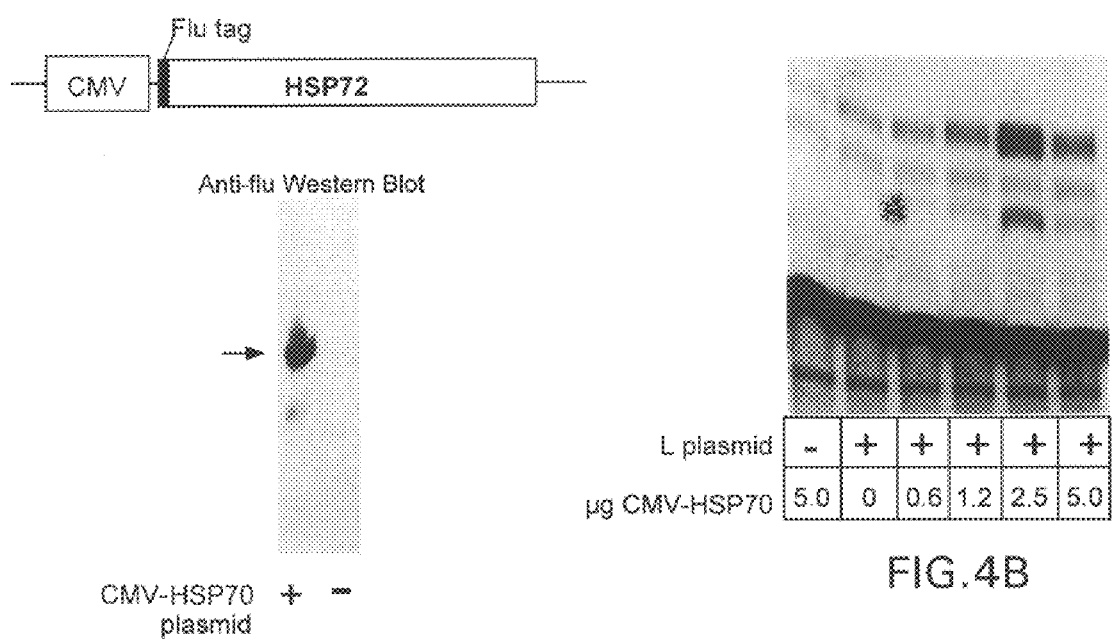
FIG. 4A is a Western Blot using antibody specific for an epitope tag, which is expressed from a CMV expression vector, in the experiments of Example 6 relating to the stimulation of minireplicon gene expression by hsp70.
FIG. 4B is an autoradiogram showing CAT assay results from cotransfection of 293-3-46 cells with the hsp70 expression vector, minireplicon DNA and L expression plasmid.

The cells were subjected to one freeze-thaw cycle to release virus, and this cell lysate was applied to a 10 cm dish containing Vero cells that were about 75% confluent. Four to five days later, the Vero cells were examined for plaques. About 2–3% of the cultures were positive for Measles virus plaques. Following the Plaque Expansion protocol outlined in Example 2, a 10–20 fold improvement was achieved over the 2% success rate just described. It appears important that the cells are not subjected to a freeze-thaw cycle prior to the plaque expansion step, as shown in Example 2.

Example 4

Heat Shock Increases Expression From Minireplicons

To examine potential mechanisms for the improved rescue results after heat shock, the effect of heat shock on gene expression from an MV minireplicon was tested (see FIG. 2 for results). The plasmid minireplicon (pMV107CAT) was designed to direct T7 RNA polymerase-mediated synthesis of a negative-sense RNA copy of the CAT gene flanked by MV termini (Sidhu et al., 1995). This plasmid was used to transfect 293-3-46 cells for intracellular synthesis of minireplicon RNA. Replication and expression of minireplicon RNA in 293-3-46 cells was carried out by complementation with MV proteins provided by infection, or complemented with an L expression plasmid because the cells provide both N and P proteins. The 293-3-46 cells were transfected overnight with MV-CAT minireplicon plasmid DNA (1 μg). Some transfections (lanes 3 and 7) also received the MV L gene expression plasmid (100 ng) to provide L complementation. About 14 hours after transfection, the media was replaced and the cells were infected with MV for 2 hours (lanes 4 and 8) with 5 pfu (plaque forming units) per cell. After infection, the media was replaced and the appropriate cell cultures (lanes 5–8) were heat shocked at 44° C. for 3 hours. Cells were harvested at 48 hours after the start of transfection and CAT assays were performed as described in the above Methods.

When examining the effect of heat shock on expression of the minireplicon, the rescue employing the heat shock produced a strong increase in CAT gene activity (FIG. 2). The experiments shown in FIG. 2 were performed with minireplicon DNA and carried out similarly to rescue experiments, except that cells were harvested 48 hours after transfection. Complementation by virus was performed by infecting transfected cells with 5 pfu per cell after removal of the transfection media. Complementation with an L expression plasmid was simply done by cotransfection with the minireplicon DNA. The results indicate that heat shock stimulates expression when either form of complementation was used. In multiple experiments, CAT expression generated by complementation with the L expression plasmid was increased from 2–10 fold by heat shock (compare lanes 3 and 7). Similarly, CAT activity was also increased when viral complementation was used and resulted in about a 5 fold enhancement (lanes 4 and 8). As expected, negative control transfections that did not receive CAT plasmid (lanes 1 and 5) or a source of L complementation (lanes 2 and 6) produced very low levels of background CAT activity.

Example 5

The possibility existed that the increased expression of the minireplicon could be related to a higher level of T7 polymerase activity after heat shock. Higher T7 polymerase activity might result from increased expression of the gene in 293-3-46 cells after heat shock. The T7 polymerase gene is expressed from the CMV immediate early promoter/enhancer in 293-3-46 cells (Radecke et al., 1995) and the CMV promoter/enhancer has been shown to respond to heat shock (Andrews, Newbound, and Lairmore, 1997). To rule out this possibility, cells were transfected with minireplicon RNA and subjected to a heat shock treatment as used in Example 4. In addition, in this example, to rule out the possibility that the effect of heat-shock was related to increased expression of the MV genes present in the 293-3-46 cell line, the RNA transfections were performed in 293 cells (Graham et al., 1977). The 293-3-46 cells do not stably express any MV genes. The transfection protocol used in this experiment was modified to accommodate RNA transfection (see Methods section above). Five μg of RNA was transfected by the calcium-phosphate procedure. MV infection of the appropriate cells was performed by adding virus immediately after the transfection mixture was added to the media. After adding the precipitate to the cells, MV (5 pfu per cell, lanes 3 and 6 of FIG. 3) was added to the culture media to initiate the infection immediately to lessen the chance of intracellular RNA degredation before it could be packaged into nucleocapsids. After a 5–6 hours transfection-infection incubation, the media was replaced and the appropriate cell samples were heat shocked 2 hours at 44° C., before being returned to 37° C. Cell extracts were prepared 24–28 hours after the start of transfection-infection for CAT assays.

The results from the RNA transfection were similar to the results of DNA transfection. Heat shock substantially increased the expression of CAT in cells that were infected (FIG. 3, compare lanes 3 and 6). No CAT activity was observed in cells that received no minireplicon RNA (lanes 1 and 4) or no viral complementation (lanes 2 and 5). The RNA transfection results also rule out the possibility that increased T7 RNA polymerase activity was responsible for the effect of heat shock in the DNA transfection experiment shown in FIG. 2.

Example 6

Stimulation of minireplicon expression by Hsp70.

Oglesbee et al. have determined that the inducible hsp70 isoform, hsp72, copurifies with CDV nucleocapsids and that these nucleocapsids display enhanced in vitro transcriptional activity (Oglesbee, Ringler, and Krakowka, 1990; Oglesbee et al., 1996). To evaluate whether hsp72 was involved in the heat shock effect that was observed in the above examples, experiments were conducted that essentially substituted overexpression of the hsp70 gene for the heat shock treatment of Example 1 (results are shown in FIG. 4). The inducible hsp70 cDNA (Hunt and Morimoto, 1985, Wu et al, 1985) was cloned from RNA prepared from heat shocked cells pursuant to Example 2. The cDNA was cloned into a CMV expression vector, plasmid pCGN (Tanaka, 1990), along with a flu epitope tag. The amino-terminus coding region of the hsp 70 gene was fused to the influenza HA epitope tag (Tanaka and 375–386., 1990), having the sequence Y P Y D V P DY A. The hsp70 cDNA was cloned to express the hsp70 protein with an amino terminus containing the HA epitope. Use of this plasmid allows one to follow the expression of the hsp70 cDNA using antibody against the influenza tag even in the presence of the background of endogenous hsp70 isoforms. Whole cell extracts prepared from transfected cells were analyzed by Western blotting (Parks and Shenk, 1996) using an antibody specific for the epitope tag (FIG. 4A). The Western analysis of extracts from transfected cells showed that the expression plasmid (FIG. 4A) produces a tagged polypeptide slightly larger 70 kD.

Cotransfection of 293-3-46 cells with the hsp70 expression vector along with the L expression plasmid and minireplicon DNA resulted in increased expression of CAT (See FIG. 4B). In this transient assay system, the overexpression of hsp70 increased the low level of L complementation by as much as 20 fold. This increase in CAT expression induced by the hsp70 expression vector is apparently specific because it requires the presence of the L polymerase plasmid and does not increase the background CAT activity observed when L is absent or the CAT plasmid is omitted from the transfection. These results strongly suggest that hsp70 is at least in part responsible for the effect of heat shock on minigenome expression.

Example 7
Heat Shock Rescue of Minireplicon Expression in Vero Cells

As a follow-up to Example 4, 293-3-46 cells were replaced by Vero cells.

Materials: For the Vero cell transfection experiments, Measles proteins N, P and L are provided by plasmiid DNAs and T7 RNA polymerase is provided by MVA/T7 (Wyatt et. al.) infection. Transfection included 100 ng of minireplicon, 400 ng N plasmid, 300 ng P plasmid, and amounts of L plasmid as shown in Table 2 below. Negative control transfections lacked L plasmid support. In addition, the Vero cells were transfected with LIPOFECTACE (purchased from Life Technologies Inc., Gaithersburg, Md.) as a transfection reagent. For each test, 2 plaque-forming units (PFU) of MVA/T7 (Wyatt et. al.) per transfection reaction are used. Two volumes of LIPOFECTACE were tested to determine the optimal amount for efficient Vero cell transfection. The transfection is performed with two different amounts of L protein expression plasmid. For heat shock, the cells are transferred to a 44° C. water bath for 3 hours. Control cells are not heat shocked.

MVA/T7: The MVA/T7 is a hybrid virus that contains one integrated copy of the T7 gene-1 under the regulation of the 11K strong late promoter (Wyatt et. al. 1995).

Expression Plasmids:

The L plasmid was provided by Radecke and Billeter. Basically, the measles L gene was cloned into the pEMC plasmid vector (Moss et al., 1990) by cloning methods disclosed by Radecke et al., (1995) to generate plasmid pEMC-La. This vector includes an internal ribosome entry site and a 3' end poly-A sequence to facilitate expression of cloned genes in eucaryotic cells. The same vector is used to prepare vectors for each of the N and P genes. The N and P protein coding regions were amplified by PCR from the measles virus genomic cDNA (Radecke et al., 1995) then cloned between the NcoI and BamHI sites of vector pEMC to generate pT7-N and pT7-P.

Vero Cell Protocol for Heat Shock:

For LIPOFECTACE AND EFFECTENE LIPOFECTACE:

Vero cells are grown in six-well culture dishes until they are approximately 50–80% confluent. The cells at about 75% confluent are desirable, because at this stage they are still rapidly dividing and healthy, and the higher cell density helps offset the cell death incurred during transfection, MVA/T7 infection and heat shock. The DNA-lipid mixture for transfection is prepared by combining DNAs (N, P, L and MV minireplicon) and 200 µl of serum-free DMEM in a microfuge tube LIPOFECTACE (12 or 15 µl depending upon experiment) was added to the DNA-media mixture and mixed gently followed by a 20 minute incubation at room temperature. At the end of the incubation, the DNA-LIPOFECTACE mixture is combined with 800 µl of serum-free DMEM containing the appropriate amount of MVA/T7 to yield a final amount of approximately 2 PFU per cell. The media is removed from the Vero cell cultures and replaced with the transfection mixture containing DNA, LIPOFECTACE and MVA/T7 The cells are incubated in a 37° C. incubator set at 5% $CO_2$ for 2–6 hours. For Vero cells, this incubation seems to be optimal at 2–3 hours. At the end of this incubation period, 1 ml of DMEM supplemented with 10% fetal bovine serum is added to the cells and the appropriate cell cultures are subjected to heat shock for 2–3 hours at 44° C. (3 hours appears optimal for Vero cells). To perform heat shock, the 6-well plate is transferred to a Ziplock plastic bag and then submersed into a 44° C. water bath. At the end of the 2–3 hour heat shock period, the cells are removed from the plastic bag and returned to the 37° C. incubator for overnight incubation. The following day, the media is replaced with 2 ml of fresh DMEM containing 10% fetal bovine serum. At approximately 48 hours after transfection, the cells are harvested to prepare extract for CAT assays or the cells are harvested and transferred to a 10 cm dish containing a monolayer of Vero cells to allow plaque expansion.

The cells were then analyzed for CAT activity. The CAT activity was stimulated about 7 fold by heat shock when used under the conditions of 12 µl of LIPOFECTACE and 100 ng L plasmid. The CAT activity was stimulated about 2 fold by heat shock when used under the conditions of 15 µl of LIPOFECTACE and 100 ng L plasmid. See Table 2 below.

TABLE 2

| Lanes | 1 | 2 | 3 | 4 | 5 | 6 | 7 | 8 | 9 | 10 | 11 | 12 |
|---|---|---|---|---|---|---|---|---|---|---|---|---|
| L ng | 0 | 100 | 200 | 0 | 100 | 200 | 0 | 100 | 200 | 0 | 100 | 200 |
| Relative Activity | — | 1.0 | 0.2 | — | 4.7 | 0.1 | — | 7.0 | 5.4 | — | 10.3 | 4.1 |
| Lipofectace (µl) | 12 | 12 | 12 | 15 | 15 | 15 | 12 | 12 | 12 | 15 | 15 | 15 |
| Heat Shock | No heat shock | | | | | | heat shock for 3h | | | | | |

Example 8
Comparing the Transfection Facilitating Reagents for Heat Shock Rescue in Vero Cells The above experiment was repeated using either LIPOFECTACE or EFFECTENE (Qiagen Inc., Valencia, Calif.).

For EFFECTENE the protocol is essentially identical except for the preparation of the DNA-lipid mixture. The DNA is mixed with 100 µl of buffered saline provided with the EFFECTENE reagent. Then 8 µl of EFFECTENE condensing reagent is added and the mixture is incubated for 5 minutes at room temperature. Next 25 µl (or amount specified in the figure) of EFFECTENE is added and the mixture is incubated for an additional 15 minutes. After the 15 minute incubation, the DNA-EFFECTENE complex is mixed with 900 µl of serum-free media containing enough MVA/T7 to provide approximately 2 PFU per cell. At this stage, application of the DNA-MVA/T7 mixture to the cells and all subsequent steps is identical to the steps followed for LIPOFECTACE.

Results are shown below in Tables 3a and 3b. (Lipo= LIPOFECTACE). Minireplicon activity was increased when heat shock was performed at 2 hours after transfection.

TABLE 3a

| Lanes | 1 | 2 | 3 | 4 | 5 | 6 | 7 | 8 | 9 | 10 | 11 | 12 |
|---|---|---|---|---|---|---|---|---|---|---|---|---|
| Relative Activity | — | 1.0 | — | 0.2 | 0.9 | 0.2 | — | 7.2 | — | 5.4 | 5.2 | 5.0 |
| Reagent ($\mu$L) | 15 | 15 | 8 | 8 | 25 | 6 | 15 | 15 | 8 | 8 | 25 | 6 |
| L Plasmid | − | + | − | + | + | + | − | + | − | + | + | + |
| Reagent Treatment | Lipo no heat shock | | Effectene | | | | Lipo heat shock at 2 h | | Effectene | | | |

TABLE 3b

| Lanes | 3 | 4 | 5 | 6 | 7 | 8 |
|---|---|---|---|---|---|---|
| Relative Act | | .8 | | .9 | .0 | .2 |
| $\mu$L of Reagent | 5 | 5 | | | 5 | |
| Reagent Treatment | Lipo | | Effectene heat shock at 6 h | | | |

Example 9
Transfecting Vero Cells with Modified Buffer Technique
Materials: BES is: {N,N-bis[2-hydroxyethyl]-2-aminoethanesulfonic acid}
Transfection of Vero cells for rescue using the BES/Calcium phosphate procedure Vero cells are grown in six-well culture dishes until they are approximately 50–80% confluent. The cells are around 75% confluent because at this stage they are still rapidly dividing and healthy, and the higher cell density helps offset the cell death incurred during transfection, MVA infection and heat shock. The day of transfection, the cells are fed with 4.5 ml of media per well and transferred to an incubator set at 37° C. (or lower for temperature if rescuing a temperature sensitive virus) and 3% $CO_2$. The media routinely used by us is DMEM supplemented with 10% fetal bovine serum (other media will work). Approximately two to four hours after feeding the cells, the transfection is initiated. The DNA-Calcium phosphate precipitates for transfection are prepared in 5 ml polypropylene tubes. DNAs for rescue, including expression plasmids for N, P, and L and the MV minireplicon are combined with water to a final volume of 225 $\mu$l. Next, 25 $\mu$l of 2.5 M $CaCl_2$ is added and the tubes are mixed gently. After preparing all of the DNA-$CaCl_2$ mixtures, the precipitates are prepared by adding 250 $\mu$l of 2×BES-Buffered saline (2×BBS: 280 mM NaCl, 1.5 mM $Na_2HPO_4$, 50 mM BES, pH 6.95–6.98). The 2×BBS is added dropwise to each tube while gently vortexing continuously during BBS addition. After adding the 2×BBS, the tubes are incubated 20 minutes at room temperature. At the end of the room temperature incubation, the 500 $\mu$l precipitates are added to the cells dropwise and the plate is rocked gently to assure mixing of the precipitates with the media. After adding the precipitates, approximately two plaque forming units (pfu) of MVA/T7 or MVA/T7-GK16 is added directly to the media and the plate is rocked gently to mix. When using GK16, a DNA synthesis inhibitor is added to the media at this stage. Either cytosine arabinoside (araC) or hydroxyurea (HU) is added to the media a 20 $\mu$g per ml or 10 mM, respectively. At 3 hours after transfection the cells are transferred to a plastic ziplock bag and submersed in a waterbath set at 44° C. for heat shock. The cells are incubated at 44° C. for 2–3 hours (the more prolonged 3 h seems to work best) then transferred back to the incubator set at 3% $CO_2$ for overnight incubation. The following day, the media and transfection components are removed from the cells and the cells are washed 2× with hepes-buffered saline (20 mM Hepes, 150 mM NaCl, 1 mM $MgCl_2$) then fresh media is added. AraC or HU is replenished in cultures that were infected with MVA/T7-GK16. The cells are incubated an additional day in an incubator set at the standard 37° C. and 5% $CO_2$ (if a temperature sensitive virus is being rescue the cells can be incubated 2 days at the appropriate lower temperature after adding fresh media). The transfected cells are then harvested for a plaque expansion step for virus rescue or harvested to prepare cell extracts for CAT assays. The transfected cells are scraped into the media and transferred to either a 10 cm plate or T25 flask containing a 50% confluent monolayer of Vero cells (or other permissive cell type of choice). The cocultured cells are incubated at 37° C. (or appropriate temperature as noted above) 4 to six hours then the media is replaced. Replacement of the media at this stage is essential when the transfected cells contained DNA synthesis inhibitors to avoid inhibiting cell growth in the coculture during the plaque expansion step. At approximately four to five days after initiating the plaque expansion step, plaques are visible and the cells can be harvested to generate a freeze-thaw lysate stock of rescued virus. Results of a CAT assay are shown on the tables 4a and 4b below. The BES/calcium phosphate procedure enhanced activity.

TABLE 4a

| Lanes | 1 | 2 | 3 | 4 | 5 | 6 |
|---|---|---|---|---|---|---|
| Relative Act | 0.11 | 1.0 | 0.16 | 1.76 | 0.16 | 2.93 |
| DNA quantity | 100 ng MVCAT 400 ng N 300 ng P 100 ng L | | 200 ng MVCAT 800 ng N 600 ng P 200 ng L | | 400 ng MVCAT 1600 ng N 1200 ng P 400 ng L | |
| L Plasmid | − | + | − | + | − | + |
| Reagent Treatment | | | LIPOFECTACE heat shock | | | |

TABLE 4b

| Lanes | 7 | 8 | 9 | 10 | 11 | 12 |
|---|---|---|---|---|---|---|
| Relative Act | 0.22 | 4.50 | 0.18 | 7.24 | 0.28 | 2.50 |
| DNA quantity | 100 ng MVCAT 400 ng N 300 ng P 100 ng L | | 200 ng MVCAT 800 ng N 600 ng P 200 ng L | | 400 ng MVCAT 1600 ng N 1200 ng P 400 ng L | |

TABLE 4b-continued

| Lanes | 7 | 8 | 9 | 10 | 11 | 12 |
|---|---|---|---|---|---|---|
| L Plasmid | – | + | – | + | – | + |
| Reagent Treatment | | | BES/calcium phosphate heat shock | | | |

For transfection techniques for the above, see Chen et al., 1987 and Tognon et al., 1996.

Example 10
Improved Rescue Based on the Use of DNA Synthesis Inhibitors and a Recombinant Modified Vaccinia Virus Ankara (MVA) that Synthesizes Bacteriophage T7 RNA Polymerase Under the Control of a Strong Early/Late Promoter Based on the foregoing, it was posited that by specifically inhibiting viral DNA replication of the helper MVA/T7 we could: 1. block all MVA/T7 growth, 2. further reduce the CPE in infected cells, and 3. enhance the efficiency of genetic rescues of RNA viruses. The inhibitors (cytosine beta-D-arabinofuranoside, AraC and/or hydroxyurea) block viral DNA synthesis, and subsequently viral intermediate and late gene expression. A recombinant MVA/T7 (MVGK16) was engineered that contains a single copy of the T7 gene-1 under the transcriptional control of the strong synthetic early/late vaccinia virus promoter. Preliminary studies, wherein MVGK16 was used as a helper virus for the genetic rescue of measles minigenomes and full length measles cDNAs, have indicated that treatment of infected cells with AraC or hydroxyurea results in an enhancement of the genetic rescue of the heterologous virus (data not shown).

Figure 6:
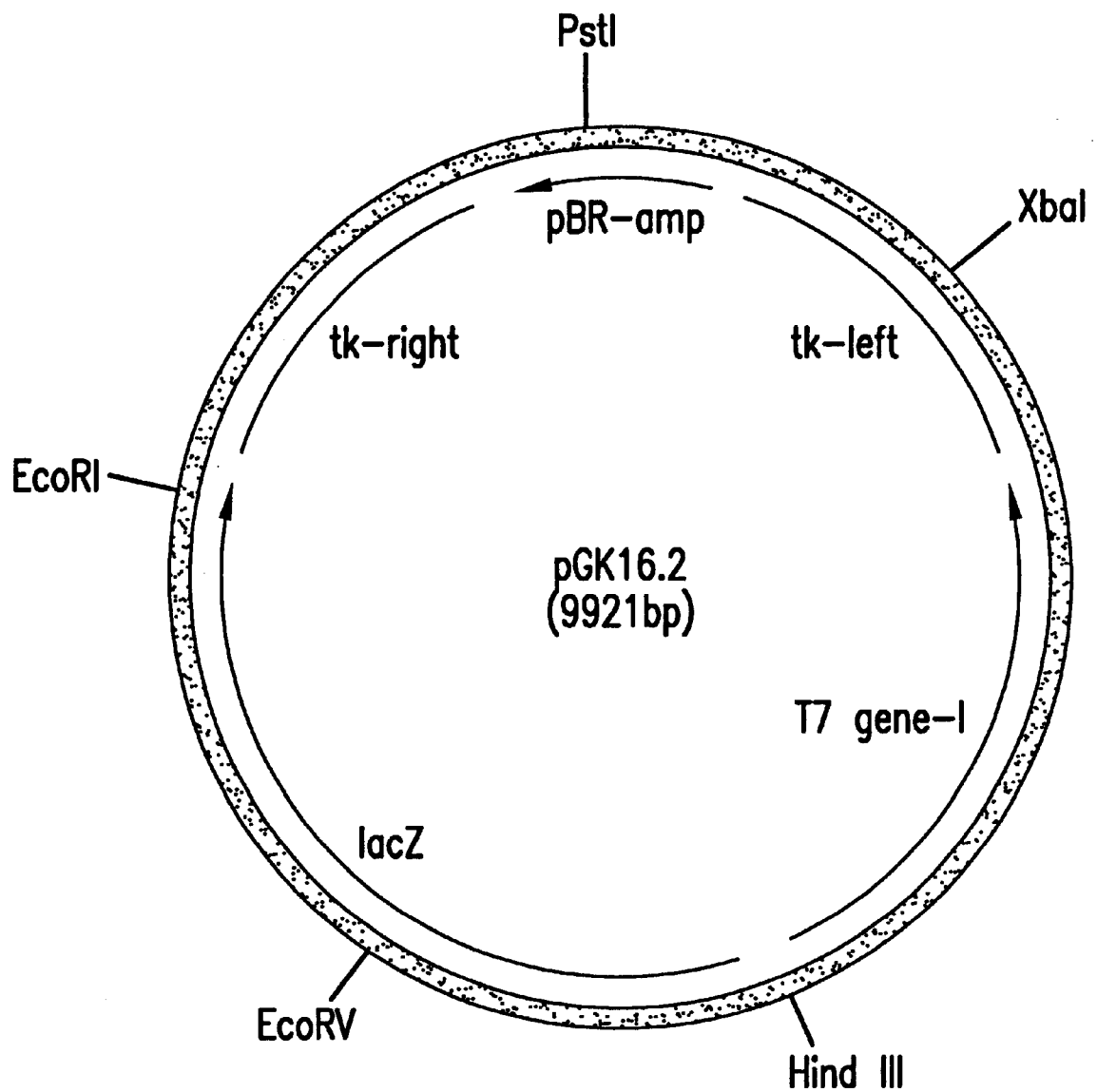
FIG. 6 is a diagram of the plasmid pGK16.2 containing a T7 gene-1 from Example 10.

Plasmids and viruses. For this study we chose the vaccinia virus pSC65 expression/recombination plasmid. This plasmid allows for expression of foreign genes under the regulation of a genetically engineered viral early/late promoter; it also provides a lacZ selection marker under the regulation of the viral 7.5K promoter. The T7 gene-1 (Moffatt et al., 1984) was excised from pT7-neo (provided by Dr. Sally Lee, Wyeth-Lederle Vaccines) as a BamHI fragment and subcloned into the BglII site of pSC65 (Chakrabarti et al., 1997), to generate pGK16.2 (FIG. 6). Recombinant plasmids were sequenced using dye terminator cycle sequencing and the 377 ABI DNA sequencer (Applied Biosystems).

Chick embryo fibroblasts (CEF; Spafas) were infected with MVA at a multiplicity of infection (MOI) equal to 0.5 plaque forming units (PFU) per cell and transfected with pGK16.2 using the DOTAP transfection-facilitating reagent (Boehringer Mannheim). Homologous recombination with MVA DNA results in interruption of the viral tk gene and insertion of the T7 gene-1 and lacZ. Recombinant viruses (MVGK16) were plaque purified three times consecutively on CEF cells using an X-gal calorimetric plaque assay. The recombinant MVGK16 was stable through three consecutive rounds of plaque purification and four rounds of amplification on CEFs as evidenced by immunostaining with rabbit polyclonal antisera against T7 polymerase and vaccinia virus (data not shown).

Genetic rescues. The BES/Calcium Phosphate procedure above was repeated with the expression system MVA/GK16, which contains the early/late promoter for T7 transcription. Modifications to the rescue protocol above for BES/Calcium Phosphate are noted herein. When using GK16, a DNA synthesis inhibitor is added to the media at this stage. Either cytosine arabinoside (araC) or hydroxyurea (HU) is added to the media at 20 μg per ml or 10 mM, respectively. The cells are incubated overnight in an incubator set at 3% $CO_2$. The transfection and heat shock are completed by following the above-protocol for the BES Example. AraC or HU is replenished in cultures that were infected with MVA/GK16. The cells are incubated an additional day in an incubator set at the standard 37° C. and 5% $CO_2$ (if a temperature sensitive virus is being rescue the cells can be incubated 2 days at the appropriate lower temperature after adding fresh media). The transfected cells are then harvested for a plaque expansion step. The transfected cells are scraped into the media and transferred to either a 10 cm plate or T25 flask containing a 50% confluent monolayer of Vero cells (or other permissive cell type of choice). The cocultured cells are incubated at 37° C. (or appropriate temperature) 4 to six hours then the media is replaced. It is particularly important to replace the media at this stage when the transfected cells contained DNA synthesis inhibitors. Inhibition of cell growth in the coculture during the plaque expansion step is not desired. At approximately four to five days after initiating the plaque expansion step, plaques should be visible and the cells can be harvested to generate a freeze-thaw lysate stock of rescued virus.

Genetic rescue experiments. The above protocol resulted in consistent improvement in the number of wells with a positive indication of rescue. See Table 5 below. Experiments are scored plus (+) or minus (–) after the first passage of recombinant virus on Vero cells. Plaque numbers in positive wells ranged from 1 to 50. All experiments contained 20 ug/ml AraC in media during overnight transfection and subsequent 24 h incubation period when MVA/T7-GK16 was used. For the experiment on Day 9, 10 mM hydroxyurea was substituted for araC DNA synthesis inhibitor.

TABLE 5

| Sample | Day 1 | Day 9 | Day 10 | Day 16 | Day 23 | Day 30 | T7 Source |
|---|---|---|---|---|---|---|---|
| 1 | + | + | – | – | – | + | MVA/T7 |
| 2 | – | + | – | + | + | + | MVA/T7 |
| 3 | + | – | – | – | – | + | MVA/T7 |
| 4 | – | – | – | – | – | + | MVA/T7 |
| 5 | + | + | – | – | – | + | MVA/T7 |
| 6 | – | + | – | – | – | – | MVA/T7 |
| 7 | + | + | + | – | + | + | MVAGK16 |
| 8 | + | + | + | + | + | + | MVAGK16 |
| 9 | + | – | + | – | + | – | MVAGK16 |
| 10 | + | + | + | – | + | + | MVAGK16 |
| 11 | + | + | + | + | + | + | MVAGK16 |
| 12 | + | + | – | – | + | + | MVAGK16 |

Provided below are a list of references which are incorporated herein.

References

Andrews, J. M., Newbound, G. C., and Lairmore, M. D. (1997). Transcriptional modulation of viral reporter gene constructs following induction of the cellular stress response. Nucleic Acids Research 25, 1082–1084.

Antoine, G., Scheiflinger, F., Dorner, F., and Falkner, F. G. The complete genomic sequence of the modified vaccinia virus Ankara strain: comparison with other orthopoxviruses. Virology. 244(2):365–96, May 1998.

Ausubel, F. M., Brent, R., Kingston, R. E., Moore, D. D., Siedman, J. G., Smith, J. A., and Struhl, K., Eds. (1987). Current Protocols in Molecular Biology. New York: Greene Publishing Associates and Wiley Interscience.

Baron, M. D., and Barrett, T. (1997). Rescue of rinderpest virus from cloned cDNA. J. Virol. 71, 1265–1271.

Blumberg, M. B., Chan, J., and Udem, S. A. (1991). Function of Paramyxovirus 3' and 5' end sequences. In "The Paramyxoviruses" (D. W. Kingsbury, Ed.), pp. 235–247. Plenum, N.Y.

Boyer, J.-C., and Haenni, A.-L. (1994). Infectious transcripts and cDNA clones of RNA viruses. Virology 198, 415–426.

Bridgen, A. and Eliott, R. M. Proc. Natl. Acad. Sci. 93, 15400–15404, 1996.

Carroll, M. W. and Moss, B. Host range and cyopathogenicity of the highly attenuated MVA strain of vaccinia virus: propagation and generation of recombinant viruses in a nonhuman mammalian cell line. Virology. 238(2): 198–211, November 1997.

Chakrabarti, S., Sister, J R, and Moss, B. Compact, synthetic, vaccinia virus early/late promoter for protein expression. BioTechniques 23:1094–1097, December 1997.

Chen, C., and H. Okayama. 1987. High-efficiency transformation of mammalian cells by plasmid DNA. Mol. Cell Biol. 7:2745–2752.

Chomczynski, P., and Sacchi., N. (1987). Single-step method of RNA isolation by acid guanidinium thiocyanate-phenol-chloroform extraction. Analytical Biochem. 162, 156–159.

Collins, P. L., Hill, M. G., Camargo, E., Grosfeld, H., Chanock, R. M., and Murphy, B. R. Production of infectious human respiratory syncytial virus from cloned cDNA confirms an essential role for the transcription elongation factor from the 5' proximal open reading frame of the M2 mRNA in gene expression and provides a capability for vaccine development. Proceedings of the National Academy of Sciences, U.S.A. 92(25):11563–11567, 1995.

Craig, E. A. (1985). The heat shock response. CRC Critical Reviews Biochem. 18, 239–280.

Drexler, I., Heller, K., Wahren., B., Erfle, V., and Sutter, G. Highly attenuated modified vaccinia virus Ankara replicates in baby hamster kidney cells, a potential host for virus propagation, but not in various human transformed and primary cells. Journal of General Virology. 79 (Pt 2):347–52, February 1998.

Enami M. and Palase P. (1991). High-efficiency formation of influenza virus transfectants. J. Virology 65, 2711–2713.

Franke, E., Yaun, H., and Luban, J. (1994). Specific incorporation of cyclophilin A into HIV-1 virions. Nature 372, 359–362.

Friedman, D., Olson, E., Georgopoulos, C., Tilly, K., Herskpwitz, I., and Banuett, F. (1984). Interactions of bacteriopahage and host macromolecules in the growth of bacteriophage lamda. Microbiol. Rev. 48, 299–335.

Garcin, D., Pelet, T., Calain, P., Sakai, Y., Shioda, T., Roux, L., Curran, J., and Kolakofsky, D. (1995). A highly recombinogenic system for the recovery of infectious Sendia paramyxovirus from cDNA; generation of a novel copyback nondefective interfering virus. EMBO J. 14, 6087–6094.

Gething, M.-J. (1996). Molecular chaperones: clasping the prize. Current Biol 6(12), 1573–1576.

Glick, B. S. (1995). Can Hsp70 proteins act as force-generating motors. Cell 80, 11–14.

Graham, F. L., Smiley, J., Russell, W. C., and Nairn, R. (1977). Characteristics of a human cell line transformed by DNA from human adenovirus 5. J. Gen. Virol. 36, 59–72.

Graham, F. L., and van der Eb, A. J. (1973). A technique for the assay of infectivity of human adenovirus DNA Virology 52, 456–467.

Gunther, E., and Walter, L. (1994). Genetic aspects of the hsp70 multigene family in vertebrates. Experientia 50, 987–1001.

He, B., Paterson, R. G., Ward, C. D., and Lamb, R. A. (1997). Recovery of infectious SV5 from cloned DNA and expression of a foreign gene. Virology 237, 249–260.

Hoffman, M. A., and Banerjee, A. K. (1997). An infectious clone of human parainfluenza virus type 3. J. Virol. 71, 4272–4277.

Horikami, S. M., and Moyer, S. A. (1991). Synthesis of leader RNA and editing of the P mRNA during transcription by purified measles virus. J. Virol. 65, 5342–5347.

Hu, J., Toft, D. O., and Seeger, C. (1997). Hepadnavirus assembly and reverse transcription require a multicomponent chaperone complex which is incorporated into nucleocapsids. EMBO J. 16, 59–68.

Hunt, C., and Morimoto, R. I. (1985). Conserved features of eukaryotic hsp70 genes revealed by comparison with the nucleotide sequence of human hsp70. Proc. Natl. Acad. Sci. USA. 82, 6455–6459.

Kato, A., et al., (1996). Genes to Cells, 1, 569–579.

Lamb, R. A., and Kolakofsky, D. (1996). Paramyxoviridae: the viruses and their replication. Third ed. In "Fields Virology" (B. N. Fields, D. M. Knipe, P. M. Howley, R. M. Chanock, T. O. Monath, J. L. Melnick, B. Roizman, and S. E. Straus, Eds.). Lippncott-Raven Publishers, Philadelphia.

Lawson, N. D., Stillman, E. A., Whitt, M. A., and Rose, J. K. (1995). Recombinant vesicular stomatitis viruses from DNA. Proc. Natl. Acad. Sci. USA. 92, 4477–4481.

Leyrer, S., Neubert, W. J., and Sedlmeier, R. Rapid and efficient recovery of Sendai virus from cDNA: factors influencing recombinant virus rescue. Journal of Virological Methods. 75(1):47–58, November 1998.

Lindquist, S. (1986). The heat-shock response. Annu. Rev. Biochem. 55, 1151–1191.

Lund, P. A. (1995). The roles of molecular chaperones in vivo. Essays in Biochemistry 29, 113–123.

Martin, J., and Hartl, F. U. (1997). Chaperone-assisted protein folding. Current opinion structural Biol 7, 41–45.

Mena et al., J. Virology, 70, 5016–5024, 1996.

Moffatt, B. A., Dunn, J. J., and Studier, F. W. Nucleotide sequence of the gene for bacteriophage T7 RNA polymerase. Journal of Molecular Biology. 173 (2): 265–9, Feb. 25, 1984.

Moss, B., O. Elroy-Stein, T. Mizukami, W. A. Alexander, and T. R. Fuerst. 1990. New mammalian expression vectors. Nature 348:91–92.

Moyer, S. A., Baker, S. C., and Horikomi, S. M. (1990). Host cell proteins required for measles virus reproduction. J. Gen. Virol. 71, 775–783.

Oglesbee, M., Ringler, S., and Krakowka, S. (1990). Interaction of canine distemper virus nucleocapsid variants with 70K heat-shock protein. J. Gen Virology 71, 1585–1590.

Oglesbee, M., Tatalick, L., Rice, J., and Krakowka, S. (1989). Isolation and characterization of canine distemper virus nucleocapsid variants. J. Gen. Virology 70, 2409–2419.

Oglesbee, M. J., Kenney, H., Kenney, T., and Krakowka, S. (1993). Enhnaced production of Morbillivirus gene-specific RNAs following induction of the cellular stress response in stable persistent infection. Virology 192, 556–567.

Oglesbee, M. J., Zheng, L., Kenney, H., and Brooks, C. L. (1996). The highly inducible member of the 70 kDa family of heat shock proteins increases canine distemper virus polymerase activity. J. Gen. Virology 77, 2125–2135.

Ogura, H., Sato, H., Kamiya, S., and Nakamura, S. (1990). Temperature elevation enhances cell surface expression of measles fusion protein in infected cells. J. Gen. Virology 71, 2475–2478.

Parks, C. L., and Shenk, T. (1996). The serotonin 1a receptor gene contains a TATA-less promoter that responds to MAZ and Sp1. J. Biol. Chem. 271, 4417–4430.

Pattnaik, A. K., Ball, L. A., LeGrone, A. W., and Wertz, G. W. (1992). Use of T7 phage polymerase and hepatits delta virus ribozyme sequences for cDNA synthesis and processing. Cell 69, 1011–20.

Pratt, W. B. (1992). Control of steroid receptor function and cytoplasmic-nuclear transport by heat shock proteins. BioEssays 14, 841–848.

Pratt, W. B., and Toft, D. O. (1997). Steroid receptor interactions with heat shock proteins and immunophilin chaperones. Endocrine reviews 18, 306–360.

Radecke, F., and Billeter, M. A. (1997). Reverse genetics meets the nonsegmented negative-strand RNA viruses. Rev. Med. Virology 7, 49–63.

Radecke, F., Spielhofer, P., Schmeider, H., Kaelin, K., Huber, M., Dotsch, C., Christiansen, G., and Billeter, M. A. (1995). Rescue of measles viruses from cloned DNA. EMBO J. 14(23), 5773–5784.

Robbins, S. J., Bussell, R. H., and Rapp, F. (1980). Isolation and partial characterization of two forms of cytoplasmic nucleocapsids from measles virus-infected cells. J. Gen. Virol. 47, 301–310.

Santoro, M. G. (1996). Viral Infection. Experientia 77, 337–357.

Schneider, H., Speilhofer, P., Kaelin, K., Dotsch, C., Radecke, F., Sutter, G., and Billeter, M. A. Rescue of measles virus using a replication-deficient vaccinia-T7 vector. Journal of Virological Methods. 64(1):57–64, February 1997.

Schnell, M. J., Mebatsion, T., and Conzelmann, K.-K. (1994). Infectious rabies viruses from cloned cDNA. EMBO J. 13, 4195–4203.

Sidhu, M. S., Chan, J., Kaelin, K., Spielhofer, P., Radecke, F., Schnieder, H., Masurekar, M., Dowling, P. C., Billeter, M. A., and Udem, S. A. (1995). Rescue of synthetic mealses virus minireplicons: measles genomic termini direct efficient expression and propagation of a reporter gene. Virology 208, 800–807.

Sutter, G., and Moss B. Nonreplicating vaccinia vector efficiently expresses recombinant genes. Proceedings of the National Academy of Sciences of the United States of America. 89(22):10847–51, Nov. 15, 1992.

Sutter, G., Ohlmann, M., and Erfle, V. Non-replicating vaccinia vector efficiently expresses bacteriophage T7 RNA polymerase. FEBS Letters. 371(1):9–12, August 1995.

Tanaka, M., and Herr, W. H. C. (1990). Differential transcriptional activation by oct-1 and oct-2: interdependent activation domains induce oct-2 phosphorylation. Cell 60, 375–386.

Tognon, M., E. M. Cattozzo, S. Bianchi, and M. G. Romanelli. 1996. Enhancement of HSV-DNA infectivity, in Vero and RS cells, by a modified calcium-phosphate transfection technique. Virus Genes 12:193–197.

Udem, S. A. (1984). Measles virus: conditions for the propagation and purification of infectious virus in high yield. J. Virological Methods 8, 123–136.

Whelan, S. P. J., Ball, L. A., Barr, J. N., and Wertz, G. T. W. (1995). Efficient recovery of infectious vesicular stomatitis virus entirely from cDNA clones. Proc. Natl. Acad. Sci. USA. 92, 8388–8392.

Wu, B., Hunt, C., and Morimoto, R. (1985). Structure and expression of the human gene encoding the major heat shock protein HSP70. Mol. Cell Biol, 5, 330–341.

Wyatt, L. S., Moss, B., and Rozenblatt, S. Replication-deficient vaccinia virus encoding bacteriophage T7 RNA polymerase for transient gene expression in mammalian cells. Virology. 210(1):202–5, Jun. 1995.

We claim:

1. A method for producing a recombinant Mononegavirales virus comprising;
    a) in at least one host cell, conducting transfection, of a rescue composition which comprises (i) a transcription vector comprising an isolated nucleic acid molecule which comprises a polynucleotide sequence encoding a genome or antigenome of a nonsegmented, negative-sense, single stranded RNA virus of the Order Mononegavirales and (ii) at least one expression vector which comprises one more isolated nucleic acid molecule(s) encoding the trans-acting proteins necessary for encapsidation, transcription and replication; under conditions sufficient to permit the co-expression of said vectors and the production of the recombinant virus; and
    b) heating the transfected rescue composition to an effective heat shock temperature under conditions sufficient to increase the recovery of the recombinant virus.

2. The method of claim 1 further comprising harvesting the recombinant virus.

3. The method of claim 1 wherein the effective heat shock temperature is above 37° C.

4. The method of claim 1 wherein the effective heat shock temperature is in the range of from 37° C. to about 50° C.

5. The method of claim 1 wherein the effective heat shock temperature is in the range of from 38° C. to about 49° C.

6. The method of claim 1 wherein the effective heat shock temperature is in the range of from 39° C. to about 48° C.

7. The method of claim 1 wherein the effective heat shock temperature is in the range of from 41° C. to about 47° C.

8. The method of claim 1 wherein the transfected cells are subjected to the effective heat shock temperature for about 5 to about 300 minutes.

9. The method of claim 1 wherein the transfected cells are subjected to the effective heat shock temperature for about 15 to about 240 minutes.

10. The method of claim 1 wherein the transfected cells are subjected to the effective heat shock temperature for about 15 to about 200 minutes.

11. The method of claim 1 wherein after step (b) the transfected rescue composition is transferred onto at least one layer of Vero cells.

12. The method of claim 11 wherein the layer of Vero cells is a monolayer.

13. The method of claim 1 wherein the RNA virus of the Order Mononegavirales is a human, bovine or murine virus.

14. The method of claim 1 wherein the isolated nucleic acid molecule encoding a genome or antigenome of a nonsegmented, negative-sense, single stranded RNA virus of the Order Mononegavirales is a chimera of more than one genome or anti-genome source.

15. The method of claim 1 wherein the isolated nucleic acid molecule encoding a genome or antigenome of a nonsegmented, negative-sense, single stranded RNA virus of the Order Mononegavirales encodes an attenuated virus or an infectious form of the virus.

16. The method of claim 1 wherein the isolated nucleic acid molecule encoding a genome or antigenome of a nonsegmented, negative-sense, single stranded RNA virus of the Order Mononegavirales encodes an infectious form of the virus.

17. The method of claim 1 wherein the isolate nucleic acid molecule encoding a genome or antigenome of a nonsegmented, negative-sense, single stranded RNA virus of the Order Mononegavirales encodes an attenuated virus.

18. The method of claim 1 wherein the isolated nucleic acid molecule encoding a genome or antigenome of a nonsegmented, negative-sense, single stranded RNA virus of the Order Mononegavirales encodes an infectious, attenuated virus.

19. The method of claim 1 wherein the RNA virus is a virus of the Paramyxoviridae Family.

20. The method of claim 1 wherein the RNA virus is a virus of the Rhabdoviridae Family.

21. The method of claim 1 wherein the RNA virus is a virus of the Filoviridae Family.

22. The method of claim 1 wherein the RNA virus is a virus selected from the group consisting of MV, RSV, PIV and BPV.

23. The method of claim 1 wherein the RNA virus is a virus MV.

24. The method of claim 1 wherein the polynucleotide encodes genome or antigenome of an RNA virus selected from the group consisting of RSV viruses and the trans-acting proteins necessary for encapsidation, transcription and replication N, P, L and M2.

25. The method of claim 1 wherein the polynucleotide encodes genome or antigenome of MV and the trans-acting proteins necessary for encapsidation, transcription and replication N, P and L.

26. The method of claim 1 wherein the polynucleotide encodes genome or antigenome of PIV-3 and the trans-acting proteins necessary for encapsidation, transcription and replication NP, P and L.

27. The method of claim 1 wherein the host cell is a prokaryotic cell.

28. The method of claim 1 wherein the host cell is a eukaryotic cell.

29. The method of claim 1 wherein the host cell is a vertebrate cell.

30. The method of claim 1 wherein the host cell is a *E. coli*.

31. The method of claim 1 wherein the host cell is derived from a human cell.

32. The method of claim 1 wherein the host cell is derived from a human embryonic cell.

33. The method of claim 1 wherein the host cell is derived from a human embryonic kidney cell.

34. The method of claim 1 wherein the host cell is derived from human embryonic cell line 293-3-46.

35. The method of claim 1 wherein the host cell is derived from human diploid primary cell lines.

36. The method of claim 1 wherein the host cell is selected from the group consisting of cells derived from Monkey diploid cells, Quasi-Primary Continuous Cell lines, CHO cell lines, MDCK cell lines, or Primary Chick Embryo Fibroblast cell lines.

37. The method of claim 1 wherein transcription vector further comprises a T7 polymerase gene.

38. The method of claim 1 wherein the rescue composition further comprises an unmodified or modified helper virus.

39. The method of claim 38 wherein the helper virus provides a T7 polymerase gene for transcription of the polynucleotide sequence encoding a genome or anti-genome of the nonsegmented, negative-sense, single stranded RNA virus.

40. The method of claim 37 wherein the T7 gene is under the regulatory control of a late promoter or an early/late promoter.

41. The method of claim 40 wherein the T7 gene is under the regulatory of an early/late promoter.

42. The method of claim 37 wherein the transfection is conducted in the presence of a DNA synthesis inhibitor.

43. The method of claim 6 wherein the RNA virus is a virus selected from the group consisting of MV, RSV, PIV and BPV.

44. The method of claim 6 wherein the RNA virus is a CDV, VSV, MV, RSV, PIV and BPV and rabies virus.

45. The method of claim 6 wherein the RNA virus is a virus of the genus Pneomovirus.

46. The method of claim 43 wherein the isolated nucleic acid molecule encoding a genome or antigenome of a nonsegmented, negative-sense, single stranded RNA virus of the Order Mononegavirales encodes an attenuated virus or an infectious form of the virus.

47. The method of claim 44 wherein the isolated nucleic acid molecule encoding a genome or antigenome of a nonsegmented, negative-sense, single stranded RNA virus of the Order Mononegavirales encodes an attenuated virus or an infectious form of the virus.

48. The method of claim 45, wherein the isolated nucleic acid molecule encoding a genome or antigenome of a nonsegmented, negative-sense, single stranded RNA virus of the Order Mononegavirales encodes an attenuated virus or an infectious form of the virus.

49. The method of claim 6 wherein the polynucleotide sequence encoding a genome or antigenome of a nonsegmented, negative-sense, single stranded RNA virus also encodes at least one heterologous gene.

50. The method of claim 44 wherein the polynucleotide sequence encoding a genome or antigenome of a nonsegmented, negative-sense, single stranded RNA virus also encodes at least one heterologous gene.

51. The method of claim 45 wherein the polynucleotide sequence encoding a genome or antigenome of a nonsegmented, negative-sense, single stranded RNA virus also encodes at least one heterologous gene.

52. The method of claim 46 wherein the polynucleotide sequence encoding a genome or antigenome of a nonsegmented, negative-sense, single stranded RNA virus also encodes at least one heterologous gene.

53. The method of claim 47 wherein the polynucleotide sequence encoding a genome or antigenome of a nonsegmented, negative-sense, single stranded RNA virus also encodes at least one heterologous gene.

54. The method of claim 48 wherein the polynucleotide sequence encoding a genome or antigenome of a nonsegmented, negative-sense, single stranded RNA virus also encodes at least one heterologous gene.

55. The method of claim 49 wherein one or more of the heterologous genes encode a co-factor, cytokine, a T-helper epitope, restriction marker, adjuvant or protein of a microbial pathogen.

56. The method of claim 55 wherein a heterologous gene encodes cytokine.

57. The method as in claim 34 wherein said method further comprises employing a transfection facilitating reagent.

58. The method as in claim 35 wherein said method further comprises employing a transfection facilitating reagent.

59. The method as in claim 36 wherein said method further comprises employing a transfection facilitating reagent.

60. The method as in claim 34 wherein the rescue composition further comprises an unmodified or modified helper virus.

61. The method as in claim 35 wherein the rescue composition further comprises an unmodified or modified helper virus.

62. The method as in claims 36 wherein the rescue composition further comprises an unmodified or modified helper virus.

63. The method of claim 60 wherein the helper virus provides a T7 polymerase gene for transcription of the polynucleotide sequence encoding the genome or antigenome of the nonsegmented, negative-sense, single stranded RNA virus and wherein the helper virus is a modified helper virus.

64. The method of claim 63 wherein said modified helper virus is a mutant of the attenuated vaccina virus.

65. The method of claim 1 wherein said method further comprises a step of transferring the transfected rescue composition onto at least one layer of plaque expansion cells.

66. A method for producing a recombinant Mononegavirales virus comprising;
   a) in at least one host cell, conducting transfection of a rescue composition which comprises (i) a transcription vector comprising an isolated nucleic acid molecule which comprises a polynucleotide encoding a genome or antigenome of a nonsegmented, negative-sense, single stranded RNA virus of the Order Mononegavirales and (ii) at least one expression vector which comprises at least one isolated nucleic acid molecule encoding the trans-acting proteins necessary for encapsidation, transcription and replication; under conditions sufficient to permit the co-expression of said vectors and the production of the recombinant virus; and
   b) transferring the transfected rescue composition onto at least one layer of plaque expansion cells.

67. The method of claim 66 wherein the layer of plague expansion cells is a monolayer.

68. The method of claim 66 further comprising harvesting the recombinant virus.

69. The method of claim 66 wherein the plaque expansion cells are at least about 50% confluent.

70. The method of claim 66 wherein the plaque expansion cells are at least about 60% confluent.

71. The method of claim 66 wherein the plaque expansion cells are at least about 75% confluent.

72. The method of claim 66 wherein the transfected cells are placed on one or more containers of plaque expansion cells such that the surface area of the Vero cells is greater than the surface area used in generating the transfected virus.

73. The method of claim 66 wherein the plaque expansion cells are Vero cells.

74. The method of claim 66 wherein the transcription vector comprises a T7 polymerase gene.

75. The method of claim 66 wherein the rescue composition further comprises an unmodified or modified helper virus.

76. The method of claim 75 wherein the helper virus provides a T7 polymerase gene for transcription of the polynucleotide sequence encoding a genome or anti-genome of the nonsegmented, negative-sense, single stranded RNA virus.

77. The method of claim 76 wherein the T7 gene is under the regulatory control of a late or an early/late promoter.

78. The method of claim 77 wherein the T7 gene is under the regulatory control of an early/late promoter.

79. The method of claim 66 wherein the transfection is conducted in the presence of a DNA synthesis inhibitor.

80. A recombinant virus prepared from any of the methods in claims 1–79.

81. A composition comprising (i) a recombinant virus of claim 1–79 and (ii) a pharmaceutically acceptable carrier.

* * * * *